(12) United States Patent
Fan et al.

(10) Patent No.: US 9,638,639 B2
(45) Date of Patent: May 2, 2017

(54) PLASMONIC-MAGNETIC BIFUNCTIONAL NANOTUBES FOR BIOLOGICAL APPLICATIONS

(71) Applicant: Board of Regents, The University of Texas System, Austin, TX (US)

(72) Inventors: Donglei Fan, Austin, TX (US); Xiaobin Xu, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 153 days.

(21) Appl. No.: 14/296,134

(22) Filed: Jun. 4, 2014

(65) Prior Publication Data

US 2014/0356411 A1 Dec. 4, 2014

Related U.S. Application Data

(60) Provisional application No. 61/830,842, filed on Jun. 4, 2013.

(51) Int. Cl.
| | |
|---|---|
| A61K 9/70 | (2006.01) |
| A61K 45/06 | (2006.01) |
| G01N 21/65 | (2006.01) |
| H01F 1/00 | (2006.01) |
| B82Y 25/00 | (2011.01) |
| A61K 9/00 | (2006.01) |

(52) U.S. Cl.
CPC ......... G01N 21/658 (2013.01); H01F 1/0063 (2013.01); A61K 9/0092 (2013.01); B82Y 25/00 (2013.01); H01F 1/0072 (2013.01); Y10T 428/2956 (2015.01)

(58) Field of Classification Search
CPC .......................... G01N 21/658; H01F 1/0063
See application file for complete search history.

(56) References Cited

U.S. PATENT DOCUMENTS

| 7,824,926 B1 | 11/2010 | Porter et al. |
| 7,829,348 B2 | 11/2010 | Porter et al. |
| 7,879,625 B1 | 2/2011 | Boss |
| 8,623,636 B2 | 1/2014 | Fernandez Lopez et al. |

OTHER PUBLICATIONS

Lin et al. (J. Mater. Chem. Published online Jul. 16, 2012; 22(35): 18314-18320).*
Sławiński et al (Langmuir. 2007; 23(20): 10357-10365).*
Grzegorz W. Sławiński ("The electrochemical synthesis, chemical synthesis, and galvanic exchange of silver nanostructures directly on surfaces." (2010). Electronic Theses and Dissertations. Paper 1341. http://dx.doi.org/10.18297/etd/1341).*
Albrecht, et al., "Anomalously intense Raman spectra of pyridine at a silver electrode" J. Am. Chem. Soc. 1977, 99, 5215-5217.
Amendola, et al., "A study of the surface plasmon resonance of silver nanoparticles by the discrete dipole approximation method: effect of shape, size, structure, and assembly. Plasmonics" Plasmonics 2010, 5, 85-97.
Anker, et al., "Biosensing with plasmonic nanosensors" Nat. Mater. 2008, 7, 442.
Bailo, et al., "Tip-enhanced Raman scattering" Chem. Soc. Rev. 2008, 37, 921.
Banholzer, et al., "Silver-Based Nanodisk Codes" ACS Nano, published online Aug. 5, 2010, 4, 5446-5452.
Banholzer, et al., "Rationally designed nanostructures for surface-enhanced Raman spectroscopy" Chem. Soc. Rev., Mar. 26, 2008, 37, 885-897.
Banholzer, et al., "On-wire lithography: synthesis, encoding and biological applications" Nature Protocols, May 14, 2009, vol. 4, No. 6, 838-848.
Blackie, et al., "Single-Molecule Surface-Enhanced Raman Spectroscopy of Nonresonant Molecules" J. Am. Chem. Soc. 2009, 131, 14466.
Böhme, et al., "Towards a specific characterisation of components on a cell surface—combined TERS-investigations of lipids and human cells" J. Raman Spectrosc, Sep. 15, 2009, 40, 1452-1457.
Camden, et al., "Probing the Structure of Single-Molecule Surface-Enhanced Raman Scattering Hot Spots" J. Am. Chem. Soc. 2008, 130, 12616.
Campion, et al., "Surface-enhanced Raman scattering" Chem. Soc. Rev. 1998, 27, 241-250.
Chen, et al., "Potential Modulated Multilayer Deposition of Multisegment Cu/Ni Nanowires with Tunable Magnetic Properties" Chem. Mater., Feb. 28, 2006, 18, 1595-1601.
Cheng, et al., "Porous Hollow Fe3O4 Nanoparticles for Targeted Delivery and Controlled Release of Cisplatin" J. Am. Chem. Soc., Aug. 5, 2009, 131, 10637.
Chien, et al., "Patterned Nanomagnets" Phys. Today, Jun. 2007, 60, 40-45.
Coluccio, et al., "Silver-based surface enhanced Raman scattering (SERS) substrate fabrication using nanolithography and site selective electroless deposition" Microelectron. Eng. 2009, 86, 1085-1088.
Das, et al., "Nano-patterned SERS substrate: Application for protein analysis vs. temperature" Biosens. Bioelectron. 2009, 24, 1693-1699—(Available online Sep. 10, 2008).
Dieringer, et al., "A Frequency Domain Existence Proof of Single-Molecule Surface-Enhanced Raman Spectroscopy" J. Am. Chem. Soc., Published on Web Dec. 1, 2007, 129, 16249-16256.
Fan, et al., "Manipulation of nanowires by ac electric fields" Appl. Phys. Lett., Nov. 1, 2004, 85, 4175-4177.
Fan, et al., "Efficiency of assembling of nanowires in suspension by AC electric fields" Appl. Phys. Lett. 2006, 89, 223115.

(Continued)

*Primary Examiner* — Scott Long
(74) *Attorney, Agent, or Firm* — Meunier Carlin & Curfman LLC

(57) ABSTRACT

The present invention includes nanotubes or rods, methods and arrays using plasmonic-magnetic bifunctional nanotubes or rods comprising: one or more silica nanotubes or rods; one or more nanomagnets embedded in a portion of the silica nanotubes or rods; and plasmonic metal nanoparticles uniformly coating in or on at least a portion of the surface of the nanomagnets and the silica nanotubes surface-coated.

10 Claims, 13 Drawing Sheets

(56) References Cited

OTHER PUBLICATIONS

Fan, et al., "Precision transport and assembling of nanowires in suspension by electric fields" Appl. Phys. Lett. 2008, 92, 093115.
Fan, et al., "Electric Tweezers" Nano Today, Available online Jul. 12, 2011, 6, 339-354.
Fan, et al., "Subcellular resolution delivery of a cytokine via precisely manipulated nanowires" Nature Nanotech, Jun. 13, 2010, 5, 545-551.
Fan, et al., "Controllable High-Speed Rotation of Metallic Nanowires" Phys. Rev. Lett., Jun. 24, 2005, 94.
Fan, et al., "Electronic Properties of Nanoentities Revealed by Mechanical Motion" Proc. Natl. Acad. Sci. 2012, 109, 9309.
Gao, et al., "Multifunctional Yolk-Shell Nanoparticles: A Potential MRI Contrast and Anticancer Agent" J. Am. Chem. Soc., published on web Aug. 6, 2008, 130, 11828-11833.
Graf, et al., "A General Method to Coat Colloidal Particles with Silica" Langmuir, published on web Jul. 11, 2003, 19, 6693-6700.
Gunnarsson, et al., "Interparticle coupling effects in nanofabricated substrates for surface-enhanced Raman scattering" Appl. Phys. Lett., Feb. 5, 2001, 78, 802-804.
Haynes, et al., "Nanosphere Lithography: A Versatile Nanofabrication Tool for Studies of Size-Dependent Nanoparticle Optics" J. Phys. Chem. B, published on web May 9, 2001, 105, 5599-5611.
Hu, et al., "Gold Nanofingers for Molecule Trapping and Detection" J. Am. Chem. Soc., published on web Aug. 26, 2010, 132, 12820-12822.
Hultgren, et al., "High-Yield Cell Separations Using Magnetic Nanowires" IEEE Trans. Magn., Jul. 4, 2004, 40, 2988-2990.
Hultgren, et al., "Cell manipulation using magnetic nanowires" J. Appl. Phys., May 15, 2003, 93, 7554-7556.
Inaba, et al., Phys. Chem. Glass.-Euro. J. Glass. Sci. Tech. Part B 2010, 51, 304.
Inaba, et al., "Non-Contact measurement of the Viscosity of a soda-lime-silica melt using electric field tweezers" Phys. Chem. Glass.-Euro. J. Glass. Sci. Tech. Part B, Dec. 2010, 51, 304-308.
Insin, et al., "Incorporation of Iron Oxide Nanoparticles and Quantum Dots into Silica Microspheres" Acs Nano 2008, 2, 197.
Jiao, et al., "Patterned nanoporous gold as an effective SERS template" Nanotech, published online Jun. 16, 2011, 22.
Jin, et al., "Multifunctional nanoparticles as coupled contrast agents" Nat. Commun 2010, 1:41.
Jones, et al., "Templated Techniques for the Synthesis and Assembly of Plasmonic Nanostructures" Chem Rev 2011, 111, 3736-3827.
Kang, et al., "Patterned Multiplex Pathogen DNA Detection by Au Particle-on-Wire SERS Sensor" Nano Lett. 2010, 10, 1189-1193.
Kleinman, et al., "Single-Molecule Surface-Enhanced Raman Spectroscopy of Crystal Violet Isotopologues: Theory and Experiment" J. Am. Chem. Soc., Feb. 24, 2011, 133, 4115-4122.
Kneipp, et al., "In Vivo Molecular Probing of Cellular Compartments with Gold Nanoparticles and Nanoaggregate" Nano Lett., published on web Sep. 23, 2006, 6, 2225-2231.
Kneipp, et al., "Single Molecule Detection Using Surface-Enhanced Raman Scattering (SER)" Phys. Rev. Lett., Mar. 3, 1997, 78, 1667.
Kneipp, et al., "Surface-enhanced Raman scattering: a new optical probe in molecular biophysics and biomedicine" Theor. Chem. Acc., published online Nov. 13, 2009, 2010, 125, 319-327.
Le Ru, et al., "Surface Enhanced Raman Scattering Enhancement Factors: A Comprehensive Study" J. Phys. Chem. C, published on web Aug. 23, 2007, 111, 13794-13803.
Lee, et al., "Hot Spots in Silver Nanowire Bundles for Surface-Enhanced Raman Spectroscopy" J. Am. Chem. Soc., published on web Jan. 26, 2006, 128, 2200-2201.
Lee, et al., "Magnetic excitations and orbital physics in the ferrimagnetic spinels MnB2O4 (B=Mn,V)" Phys. Rev. B, Feb. 8, 2008, 77.
Levin, et al., "Magnetic-plasmonic Core-Shell Nanoparticles" Acs Nano 2009, vol. 3, No. 6, 1379-1388.
Lim, et al., "Plasmonic Magnetic Nanostructure for Bimodal Imaging and Photonic-Based Therapy of Cancer Cells" Chembiochem 2007, 8, 2204-2209.
Lim, et al., "Nanogap-engineerable Raman-active nanodumbbells for single-molecule detection" Nature Mater., published online Dec. 13, 2009, 9, 60-67.
Lim, et al., "Highly uniform and reproducible surface—enhanced Raman scattering from DNA—tailorable nanoparticles with 1—nm interior gap" Nat. Nanotech., Jul. 2011, 6, 452-460.
Link, et al., "Size and Temperature Dependence of the Plasmon Absorption of Colloidal Gold Nanoparticles" J. Phys. Chem. B 1999, 103, 4212-4217.
Liu, et al., "Red shift of plasmon resonance frequency due to the interacting Ag nanoparticles embedded in single crystal SiO 2 by implantation" Appl. Phys. Lett. 1998, Apr. 13, 1998, 72, 1823-1825.
Liusman, et al., "Free-Standing Bimetallic Nanorings and Nanoring Arrays Made by On-Wire Lithography" Acs Nano, published online Nov. 11, 2010, 4, 7676.
McMahon, et al., "Gold nanoparticle dimer plasmonics: finite element method calculations of the electromagnetic enhancement to surface-enhanced Raman spectroscopy" Anal Bioanal Chem 2009, 394, 1819-1825.
Michaels, et al., "Surface Enhanced Raman Spectroscopy of Individual Rhodamine 6G Molecules on Large Ag Nanocrystals" J. Am. Chem. Soc., published online Mar. 22, 1999, 121, 9932-9939.
Michaels, et al., "Ag Nanocrystal Junctions as the Site for Surface-Enhanced Raman Scattering of Single Rhodamine 6G Molecules" J. Phys. Chem. B, published on web Nov. 23, 2000, 104, 11965-11971.
Moskovits, M., "Imaging: Spot the hotspot" Nature, Jan. 20, 2011, 469, 307-308.
Nie, et al., "Probing Single Molecules and Single Nanoparticles by Surface-Enhanced Raman Scattering" Science, Feb. 21, 1997, 275, 1102-1106.
Oran, et al., "Nanofabricated periodic arrays of silver elliptical discs as SERS substrates" J. Raman Spectrosc., published online Jun. 13, 2008, 39, 1811-1820.
Ou, et al., "Hot-Spot Engineering in Polygonal Nanofinger Assemblies for Surface Enhanced Raman Spectroscopy" Nano Lett., May 23, 2011, 11, 2538-2542.
Park, et al., "Synthesis and size control of monodisperse copper nanoparticles by polyol method" J. Colloid Interface Sci., available online Mar. 24, 2007, 311, 417-424.
Peng, et al., "Plasmonic/Magnetic Bifunctional Nanoparticles" Angew. Chem. Int. Edit. 2011, 50, 3158-3163.
Qian, et al., "Single-molecule and single-nanoparticle SERS: from fundamental mechanisms to biomedical applications" Chem. Soc. Rev., published on the web Mar. 26, 2008, 37, 912-920.
Qin, et al., "Nanodisk Codes" Nano Lett., Nov. 28, 2007, 7, 3849-3853.
Qin, et al., "Designing, fabricating, and imaging Raman hot spots" Proc. Nat. Acad. Sci. USA, Sep. 5, 2006, 103, 13300-13303.
Qin, et al., "On-Wire Lithography" Science, Jul. 1, 2005, 309, 113-115.
Schmidt, et al., "Nanopillars: Large Area Fabrication of Leaning Silicon Nanopillars for Surface Enhanced Raman Spectroscopy" Adv. Mater. 2012, 24, OP11.
Smythe, et al., "Optical Antenna Arrays on a Fiber Facet for In Situ Surface-Enhanced Raman Scattering Detection" Nano Lett., Mar. 2009, 9, 1132-1138.
Sniadecki, et al., "Magnetic microposts for mechanical stimulation of biological cells: Fabrication, characterization, and analysis" Rev. Sci. Instrum. 2008, 79.
Sotiriou, et al., "Hybrid, Silica-Coated, Janus-Like Plasmonic-Magnetic Nanoparticles" Chem. Mater., published Mar. 9, 2011, 23, 1985-1992.
Stranahan, et al., "Super-resolution Optical Imaging of Single-Molecule SERS Hot Spots" Nano Lett., published on web Aug. 18, 2010, 10, 3777.
Temnov, et al., "Active magneto-plasmonics in hybrid metal—ferromagnet structures" Nat. Photonics, published online Jan. 17, 2010, 4, 107-111.
Weber, et al., "Super-Resolution Imaging Reveals a Difference between SERS and Luminescence Centroids" ACS Nano 6, 1839-1848 (published online Jan. 16, 2012).
Wei, et al., "Plasmon Resonance of Finite One-Dimensional Au Nanoparticle Chains" Nano Lett, 2004, 4: 1067-1071.

(56) References Cited

OTHER PUBLICATIONS

Weng, et al., "Targeted Tumor Cell Internalization and Imaging of Multifunctional Quantum Dot-Conjugated Immunoliposomes in Vitro and in Vivo" Nano Lett. 8, 2851-2857 (published on web Aug. 20, 2008).

Xu, et al., "Ordered Arrays of Raman Nanosensors for Ultrasensitive and Location Predictable Biochemical Detection" Adv. Mater. 2012, 24, 5457-5463.

Xu, et al., "Au-Fe3O4 Dumbbell Nanoparticles as Dual-Functional Probes" Angew. Chem. Int. Edit. 2008, 47, 173-176.

Xu, et al., "Guided-mode-resonance-coupled plasmonic-active SiO2 nanotubes for surface enhanced Raman spectroscopy" Appl. Phys. Lett. 2012, 100, 191114.

Xu, et al., "Magnetic Core/Shell Fe3O4/Au and Fe3O4/Au/Ag Nanoparticles with Tunable Plasmonic Properties" J. Am. Chem. Soc. 2007, 129, 8698-8699.

Xu, et al., "Dumbbell-Like Au-Fe3O4 Nanoparticles for Target-Specific Platin Delivery" J. Am. Chem. Soc., Apr. 1, 2009, 131, 4216-4217.

Xu, Hongxing "Theoretical study of coated spherical metallic nanoparticles for single-molecule surface-enhanced spectroscopy" Appl. Phys. Lett., Dec. 13, 2004, 85, 5980-5982.

Yi, et al., "Silica-Coated Nanocomposites of Magnetic Nanoparticles and Quantum Dots" J. Am. Chem. Soc., Published on web Mar. 15, 2005, 127, 4990-4991.

Zheng, et al., "Complementary Electrical and Spectroscopic Detection Assays with On-Wire-Lithography-Based Nanostructures" Small 2009, 5, No. 22, 2537-2540.

Zhu, et al., "Stimuli-Responsive Controlled Drug Release from a Hollow Mesoporous Silica Sphere/Polyelectrolyte Multilayer Core-Shell Structure" Angew. Chem. Int. Edit. 2005, 44, 5083-5087.

\* cited by examiner

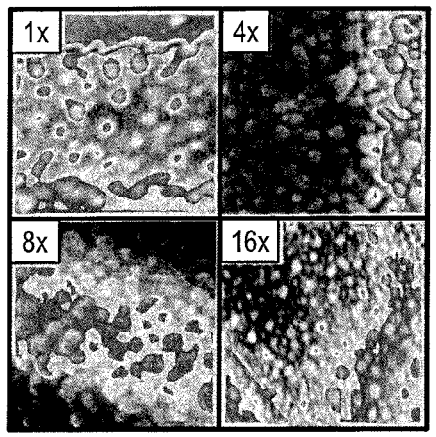 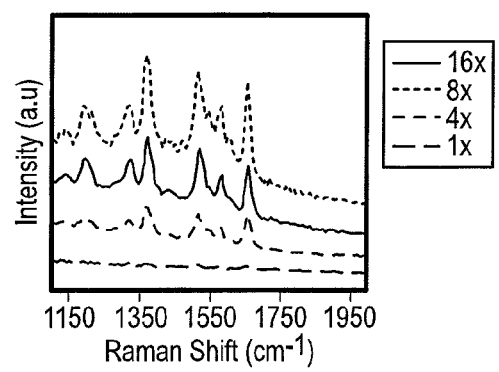
*FIG. 4A*  *FIG. 4B*
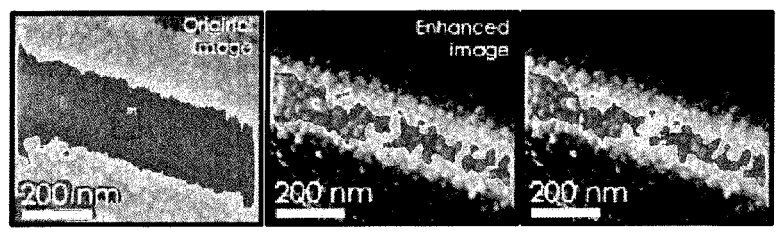
*FIG. 5A*
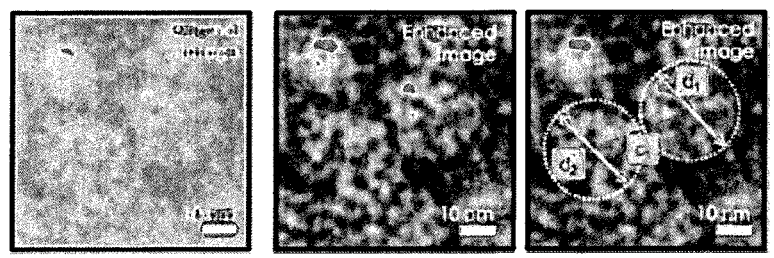
*FIG. 5B*

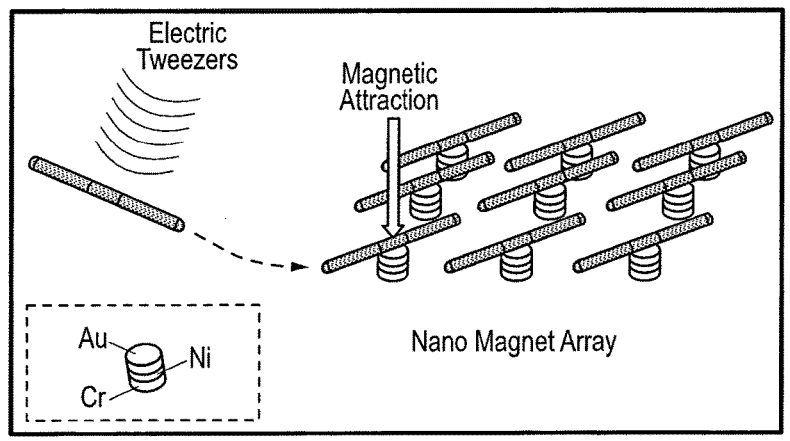
*FIG. 9*
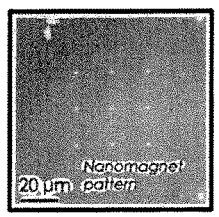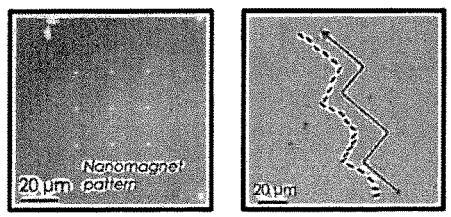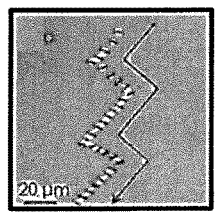
*FIG. 10A*  *FIG. 10B*  *FIG. 10C*
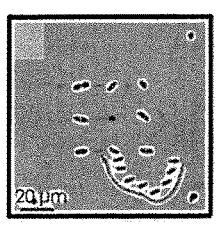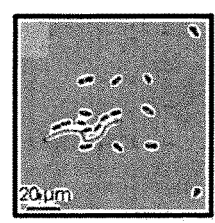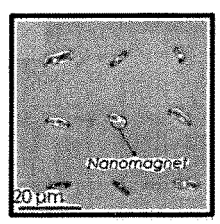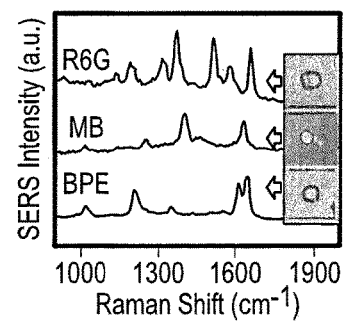
*FIG. 10D*  *FIG. 10E*  *FIG. 10F*
*FIG. 10G*

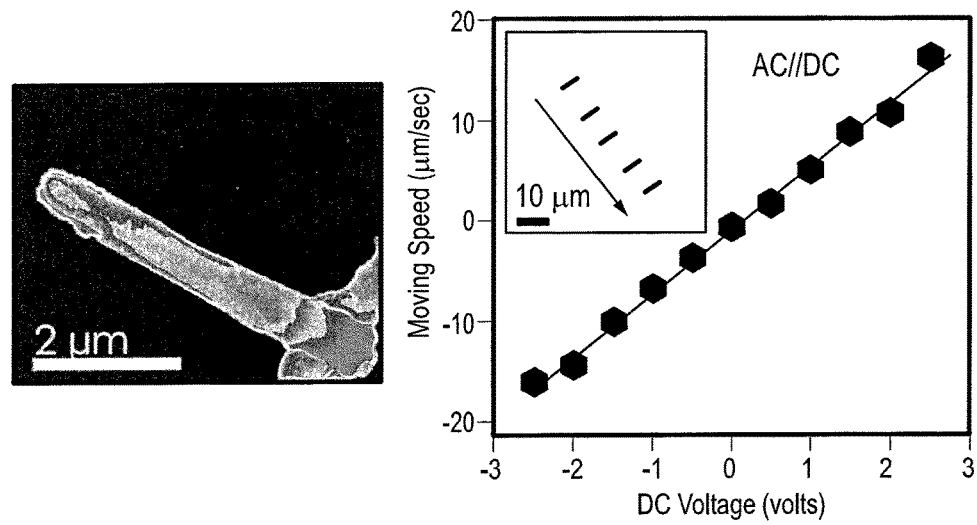
*FIG. 11*
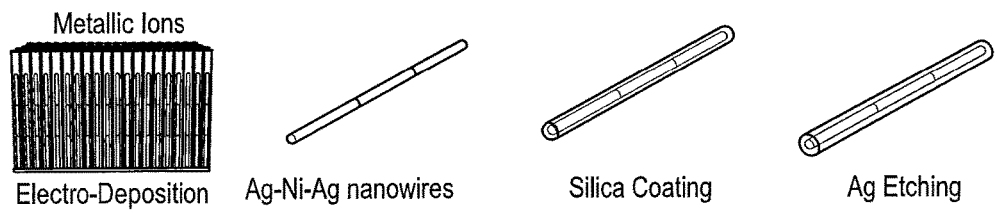
*FIG. 12A*   *FIG. 12B*   *FIG. 12C*
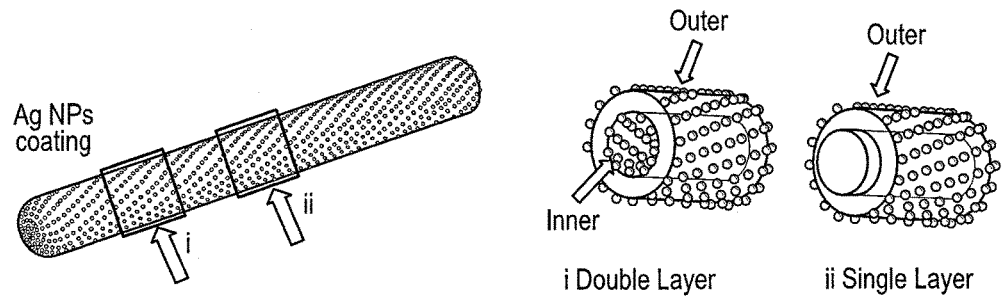
*FIG. 12D*

PLASMONIC-MAGNETIC BIFUNCTIONAL NANOTUBES FOR BIOLOGICAL APPLICATIONS

CROSS-REFERENCE TO RELATED APPLICATIONS

This application claims priority to U.S. Provisional Application Ser. No. 61/830,842, filed Jun. 4, 2013, the entire contents of which are incorporated herein by reference.

STATEMENT OF FEDERALLY FUNDED RESEARCH

This invention was made with government support under Grant no. R41 EB012885 awarded by the National Institutes of Health; and Grant no. 1150767 awarded by the National Science Foundation. The government has certain rights in the invention.

TECHNICAL FIELD OF THE INVENTION

The present invention relates in general to the field of sensors, and more particularly, to novel plasmonic-magnetic bifunctional nanotubes for biological applications.

BACKGROUND OF THE INVENTION

Without limiting the scope of the invention, its background is described in connection with Raman sensors.

One example is taught in U.S. Pat. No. 7,879,625, issued to Boss for the preparation of SERS substrates on silica-coated magnetic microspheres. Briefly, this patent discloses improved surface-enhanced Raman scattering (SERS) substrates that are said to comprise chemically-derivatized magnetic microparticles complexed with metal colloidal particles or substrates. The SERS substrates are said to permit collection, detection, measurement, and/or analysis of analytes present at concentrations ranging parts per trillion to parts per billion. The compositions, methods, and devices taught are also said to provide for rapid and/or sensitive detection of chemical compounds of interest present in small concentrations. The SERS substrates on silica-coated magnetic microspheres are said to allow the detection of trace samples including, for example, BTEX (benzene, toluene, ethylbenzene, and xylenes), chlorinated solvents, TNT, nerve agents, blister agents, metal ions, anions, antigens, peptides, nucleic acids, spores, fungi, viruses, and bacteria.

Two more examples are taught in U.S. Pat. Nos. 7,829,348 and 7,824,926, issued to Porter, et al., for Raman-active reagents and the use thereof. Briefly, these patents are said to provide Raman-active reagents for use in biological and other applications, methods and kits for their use, and manufacture. Porter teaches a Raman-active reporter molecule, a binding molecule, and a surface-enhancing particle that causes surface enhanced Raman scattering (SERS). The Raman-active reporter molecules and the binding molecules are affixed to the particle to give both a strong SERS signal and to provide biological functionality, e.g., antigen or drug recognition. The Raman-active reagents are said to function as an alternative to fluorescence-labeled reagents, and have the advantage of having: improved signal stability, sensitivity, and the ability to simultaneously detect several biological materials. The Raman-active reagents also said to have a wide range of applications, especially in clinical fields (e.g., immunoassays, imaging, and drug screening).

Another example is taught in United States Patent Application Publication No. 2013/0040292, filed by Fernandez Lopez, et al., and is directed to nanoparticle biosensor, method of preparing same and uses thereof. Briefly, this application is said to teach nanoparticle biosensors comprising: a magnetic core, a silica layer, one or more outer metal layers which can be of different types and deposited in an alternating manner and immobilized on the outer surface, and a layer of synthetic or natural organic or inorganic biosensor molecules that can bind to biomolecules. The invention also relates to a method of obtaining the nanoparticle biosensors as well as to the different uses thereof.

SUMMARY OF THE INVENTION

In one embodiment, the present invention includes a plasmonic-magnetic bifunctional nanotubes or nanorods comprising: one or more silica nanotubes or nanorods; one or more nanomagnets embedded in a portion of the silica nanotubes or nanorods; and plasmonic metal nanoparticles uniformly coating in, on, or about, at least a portion of the surface of the nanomagnets and the silica nanotubes surface-coated. In one aspect, the nanotubes provide a density of hotspots of 100, 200, 300, 400, 500, 600, 700, 800, 900, 1,000, 1,500, 2,000, 2,500, 3,000, 4,000 or 5000/$\mu m^2$ for surface enhanced Raman scattering (SERS). In another aspect, a diameter of the nanotubes or nanorods can be tuned to between 10 nm to 1 cm, 20 nm to 0.5 cm, 50 nm to 0.1 cm, 75 nm to 0.5 cm, 100 nm to 0.01 cm, 100 nm to 1 µm. In another aspect, the silica shell thickness of the nanotubes or nanorods can be tuned to between 10 nm to 1 cm, 20 nm to 0.5 cm, 50 nm to 0.1 cm, 75 nm to 0.5 cm, 100 nm to 0.01 cm, 100 nm to 1 µm any desirable dimension without limitation. In another aspect, the total length of the plasmonic nanotubes or nanorods to between 10 nm to 1 cm, 20 nm to 0.5 cm, 50 nm to 0.1 cm, 75 nm to 0.5 cm, 100 nm to 0.01 cm, 100 nm to 1 µm. In another aspect, the nanotubes provide a density of hotspots of up to 5000/$\mu m^2$ for surface enhanced Raman scattering (SERS) and an enhancement factor (EF) in the range of $10^4$ to $10^{11}$. In another aspect, the plasmonic NPs coated on the entire surface of the nanotubes provide large and uniform SERS EF, wherein single-molecule events can be repeatedly detected. In another aspect, a magnetic anisotropy of the nanotubes is caused by the embedded nanomagnets, wherein the bifunctional nanotubes can be tuned to be parallel or vertical to the long direction of the nanotubes for nano-manipulation. In another aspect, the nanotubes area capable of magnetically delivery to a single living mammalian cell. In another aspect, the nanotubes can be assembled on designated locations for position predictable analysis via the embedded nanomagnets. In another aspect, the nanotubes are adapted for at least one of single-cell bioanalysis, biochemical detection, imaging-contrast enhancement, magnetic manipulation, magnetic separation, and biosubstance delivery. In another aspect, the entire surface of the nanotubes and the embedded nanomagnets is coated. In another aspect, the plasmonic metal nanoparticles comprise at least one of silver, gold, cobalt, rhodium, iridium, copper, platinum, or palladium. In another aspect, the nanocomposite further comprises a metallic rod within the silica nanotube. In another aspect, the method further comprises a metallic rod within the silica nanotube, wherein the metallic rod is defined further as a nanorod comprising a tri-layer structure of Ag/Ni/Ag. In another aspect, the nanocomposite further comprises a metallic rod within the silica nanotube, wherein the metallic rod can be made of any materials such as Ni. In another aspect, the nanocomposites are surface functionalized to bind an active agent. In another aspect, the nanocomposites are integrated into a micro- or a nano-mechanical device.

In another embodiment, the present invention includes a method of making a plasmonic-magnetic bifunctional nanotube comprising: forming a silica rod or tube; embedding a magnetic material in the silica rod, thereby providing a magnetic moment to the rod or tube; and coating at least a portion of the silica rod or tube with a metallic coating, wherein the nanotube is plasmonic-magnetic. In one aspect, the metallic coating is deposited chemically, by chemical vapor deposition, sputtering, or ion implantation. In another aspect, the thickness of the metallic coating is optimized. In another aspect, the nanotubes provide a density of hotspots of 100, 200, 300, 400, 500, 600, 700, 800, 900, 1,000, 1,500, 2,000, 2,500, 3,000, 4,000 or 5000/$\mu m^2$ for surface enhanced Raman scattering (SERS). In another aspect, the nanotubes provide a density of hotspots of up to 5000/$\mu m^2$ for surface enhanced Raman scattering (SERS) and an enhancement factor (EF) of $3.8 \times 10^{10}$. In another aspect, the plasmonic NPs coated on the entire surface of the nanotubes provide large and uniform SERS EF. Single-molecule events can be repeatedly detected. In another aspect, a magnetic anisotropy of the nanotubes is caused by the embedded nanomagnets and the bifunctional nanotubes can be tuned to be parallel or vertical to the long direction of the nanotubes for nano-manipulation. In another aspect, a magnetic anisotropy can be controlled by tuning the aspect ratio of Ni segments, whereby the aspect ratio (in the direction of the nanowires) is lower than 1, wherein the magnetization direction of Ni is vertical to the long-axis of the nanorod/nanotube. In another aspect, a magnetic anisotropy can be controlled by tuning the aspect ratio of Ni segments, whereby the aspect ratio is higher than 2, wherein the magnetization direction of Ni is along the long-axis of the nanorod/nanotube. In another aspect, the nanotubes area capable of magnetically delivery to a single living mammalian cell. In another aspect, the nanotubes can be assembled on designated locations for position predictable analysis via the embedded nanomagnets. In another aspect, the nanotubes are capable of sensing without the embedded magnet. In another aspect, the nanotubes are adapted for at least one of single-cell bioanalysis, biochemical detection, imaging-contrast enhancement, magnetic manipulation, magnetic separation, and biosubstance delivery. In another aspect, the entire surface of the nanotubes and the embedded nanomagnets is coated. In another aspect, the plasmonic metal nanoparticles comprise at least one of silver, gold, cobalt, rhodium, iridium, copper, platinum, or palladium. In another aspect, the nanotube further comprising a nanorod or nanotube within the silica rod or tube, wherein the nanorod or nanotube is magnetic. In another aspect, the nanotube further comprising a nanorod or nanotube within the silica rod or tube, wherein the nanorod or nanotube comprising a tri-layer structure of Ag/Ni/Ag. In another aspect, the nanotube further comprising a nanorod or nanotube within the silica rod or tube, wherein the nanorod or nanotube comprises, e.g., Ni. In another aspect, the nanocomposites are surface functionalized to bind an active agent. In another aspect, the nanocomposites are integrated into a micro- or a nano-mechanical device.

Yet another embodiment of the present invention includes a nanosensor array comprising: two or more plasmonic-magnetic bifunctional nanotubes, wherein each of the Plasmonic-magnetic bifunctional nanotubes further comprises one or more analyte detectors, wherein binding of the analyte to the analyte detector on the plasmonic-magnetic bifunctional nanotubes is detected. In one aspect, the array is formed by assembly of the two or more plasmonic-magnetic bifunctional nanotubes into a pre-designed array with one or more electric fields.

Yet another embodiment of the present invention includes a steerable, controllable plasmonic-magnetic bifunctional active agent delivery device comprising: one or more silica nanotubes or nanorods comprising an active agent; one or more nanomagnets embedded in a portion of the silica nanotubes or nanorods; and plasmonic metal nanoparticles uniformly coating in, on, or about, at least a portion of the surface of the nanomagnets and the silica nanotubes surface-coated, wherein the plasmonic-magnetic bifunctional nanotubes or nanorods can be steered three-dimensionally in a liquid medium. In another aspect, the nanocomposites are surface functionalized to bind an active agent. In another aspect, the nanocomposites are integrated into a micro- or a nano-mechanical device. In another aspect, one or more active agents are bound to the nanocomposites that are integrated into a micro- or nano-mechanical device, and wherein a mechanical force is applied to release the one or more active agents.

BRIEF DESCRIPTION OF THE DRAWINGS

For a more complete understanding of the features and advantages of the present invention, reference is now made to the detailed description of the invention along with the accompanying figures and in which:

FIGS. 4A and 4B are (4a) SEM images of nanocapsules prepared under different conditions (1×, 4×, 8×, 16×). Each image has an area of 300 nm×300 nm. (b) Detection of R6G-SERS spectra from different samples (1×, 4×, 8×, 16×).

FIGS. 5A and 5B show the characterization of size distribution of NPs. (5a) Enhanced SEM images from FIG. 3(b-c), where the region in the red dotted square is magnified to show the characterization in (5b).

FIGS. 6A to 6C show the: (6A) Size distributions of Ag NPs. (6B) Estimation of junction size distribution and (6C) junction/hotspot density by taking different cut-off junction sizes. Measurements are based on the rectangle highlighted region (0.07 $\mu m^2$) from FIG. 5a.

FIG. 9 shows that using electric tweezers, nanocapsules can be transported and assembled onto a pre-patterned array of nanomagnets by utilizing the magnetic attraction force between the Ni segments in the nanocapsules and the magnetic layers inside the nanomagnets.

FIGS. 10A to 10G show that the nanocapsules of the present invention can be precisely transported and assembled on the nanomagnets with electric tweezers. (10A) A 3×3 array of nanomagnets fabricated using E-beam lithography. With combined AC and DC E fields applied in both X and Y directions, nanocapsules were transported along prescribed trajectories such as "stairs" with (10B) parallel and (10C) transverse orientations. (10D, 10E) Overlapped snapshots show the assembling process of a nanocapsule, where the nanomagnets were highlighted in red. The nanocapsules can be maneuvered and positioned at designated positions, showing the high flexibility and precision of the assembling. (10F) An assembled 3×3 nanocapsules array. The bright nanomagnets are in the center of the nanocapsules, indicating that the attachment is due to the magnetic attraction between the Ni segments in the center of the nanocapsules and the magnetic layers in the patterned magnets. All the images were taken by reflective optical imaging. (10G) From assembled nanocapsules, various chemicals were detected including rhodamine 6-G (R6G), methylene blue, and BPE.

FIG. 11 shows (left) an SEM image of a hollow plasmonic nanotube; (right) hollow nanotubes being transported by a DC E field; however, the orientations of the nanotubes could not be controlled by the AC E field due to the weak polarization and low alignment torques of the insulating silica nanotubes in an AC E field. For example, when AC//DC, the nanotubes cannot be aligned parallel to the moving direction.

FIGS. 12A to 12D show an example of schematics of fabrication of PM nanotubes. (12A) Electrodeposition of Ag/Ni/Ag nanowires. (12B) Silica shells coating. (12C) Etching of Ag segment to get hollow nanotubes with solid Ni embedment. (12D) Synthesis of Ag NPs on both the inner and outer surfaces of nanotubes. (Inserts are cross-section view of (i) the hollow segment and (ii) the Ni embedded segment of the PM nanotubes.)

FIG. 21A illustrates the rotation controlled release of biochemicals (the motor fixed on the nanomagnet is SERS sensitive, which is a silica shelled Au—Ni—Au nanowire with uniform surface distributed Ag nanoparticles). The nanomotor is functionalized with Nile blue (shown as dots surrounding the central nanorod). In FIG. 21B the release rate k monotonically increases with the rotation speeds of nanomotors.

DETAILED DESCRIPTION OF THE INVENTION

Figure 1:
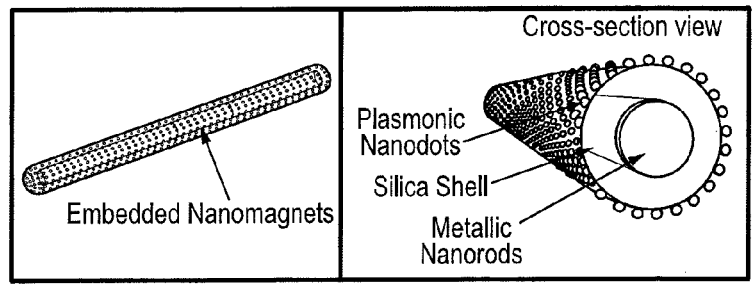
FIG. 1 shows one structure for a tri-layer nanocapsule.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "active agent," "biosubstance," "active ingredient(s)," "pharmaceutical ingredient(s)," and "bioactive agent" are defined as small molecules, medium to macromolecules (e.g., siRNA, miRNA, DNA binding proteins, enzyme agonists or antagonists, enzymes, kinases, phosphatases, lipases, nucleases, proteases), drugs and/or pharmaceutically active ingredients, nano, micro or milli MEMS devices, or detectable labels. The present invention may be used to encapsulate, attach, bind or otherwise be used to affect the storage, stability, longevity and/or release of any of the following drugs as the pharmaceutically active agent in a composition.

Non-limiting examples of active agents include, but are not limited to, antibiotics, analgesics, vaccines, anticonvulsants; antidiabetic agents, antifungal agents, antineoplastic agents, antiparkinsonian agents, antirheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, antihypertensive, hyperthyroids, antihyperthyroids, anti-asthmatics and vertigo agents. In certain embodiments, the one or more therapeutic compounds are water-soluble, poorly water-soluble drug or a drug with a low, medium or high melting point. The therapeutic compounds may be provided with or without a stabilizing salt or salts.

Active Agents

One or more of the following active agents may be combined with one or more carriers and the present invention (which may itself be the carrier): analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like.

Decongestants such as phenylephrine, ephedrine, naphazoline, tetrahydrozoline, and the like.

Antipyretics such as aspirin, salicylamide, non-steroidal anti-inflammatory agents, and the like. Antimigrane agents such as, dihydroergotamine, pizotyline, and the like.

Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprofen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like.

Steroids such as, androgenic steroids, such as testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β$_2$-adrenergic agonists, such as, albuterol, terbutaline, metaproterenol, ritodrine, carbuterol, fenoterol, quinterenol, rimiterol, solmefamol, soterenol, tetroquinol, and the like.

Sympathomimetics such as, dopamine, norepinephrine, phenylpropanolamine, phenylephrine, pseudoephedrine, amphetamine, propylhexedrine, arecoline, and the like.

Local anesthetics such as, benzocaine, procaine, dibucaine, lidocaine, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE$_1$, PGE$_2$α, and PGF$_2$α, and the PGE$_1$ analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenytoin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Muscle relaxants such as, tolperisone, baclofen, dantrolene sodium, cyclobenzaprine.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like.

Anti-malarials such as, the 4-aminoquinolines, alphaaminoquinolines, chloroquine, pyrimethamine, and the like.

Anti-ulcerative agents such as, misoprostol, omeprazole, enprostil, and the like.

Antiulcer agents such as, allantoin, aldioxa, alcloxa, N-methylscopolamine methylsuflate, and the like. Antidiabetics such as, insulin, and the like.

For use with vaccines, one or more antigens, such as, natural, heat-killer, inactivated, synthetic, peptides and even T cell epitopes (e.g., GADE, DAGE, MAGE, etc.) and the like.

The drugs mentioned above may be used in combination as required. Moreover, the above drugs may be used either in the free form or, if capable of forming salts, in the form of a salt with a suitable acid or base. If the drugs have a carboxyl group, their esters may be employed.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like.

When a drug different than an anesthetic agent is used the solvent selected is one in that the drug is soluble. In generally the polyhydric alcohol may be used as a solvent for a wide variety of drugs. Other useful solvents are those known to solubilize the drugs in question.

Localized surface plasmon resonance (LSPR), owing to collective oscillation of conduction-band electrons in noble-metal (Au, Ag) nanostructures, induces greatly enhanced electric (E) fields in confined nanoscale locations, such as on the tips of nanorods or in the junctions of nanodimers.[1] These locations are called hot spots. In the vicinity of hot spots, Raman scattering spectra of biochemicals can be substantially amplified with $E^4$ dependence due to E-field enhancement of both the incident light and Raman scattering spectra.[1c] This phenomenon is called Surface Enhanced Raman Scattering (SERS)[2] and has drawn intensive research interest due to the potential applications in label-free and multiplex biochemical detection.[3] The effect of SERS is so pronounced that the enhancement factor (EF) can reach $10^{10}$ at the junctions of Ag nanoparticles,[4] where single-molecule events can be readily observed.[1c, 4a, 5] However, the practical applications of SERS for ultrasensitive biochemical detection is still challenging because (1) it is difficult to create a large number of hotspots with controlled junctions at a low cost for sensitive and relatively reproducible detection[6]. (2) It is even more arduous to flexibly assemble the hotspots at desirable positions for location predicable sensing.

Previous research in biochemical detection with SERS spectroscopy utilized aggregates of colloidal plasmonic nanoparticles, where the hotspots are random in dimensions, quantity, and location by nature.[7] The recent breakthrough of On-Wire Lithography (OWL)[8] has made it possible to control the gap sizes of metallic nanodisk/rod pairs to a few nanometers and has demonstrated single-molecule sensitivity for various biochemicals such as methylene blue,[1d] p-mercaptoaniline,[9] and Cy-3-labeled DNA.[10] However, the OWL applications are still limited by the low density of hot spots. Other methods including E-beam lithography,[11] nanosphere/colloidal lithography[12], and porous template assisted deposition[13] were explored for sensitive and location-predictable SERS sensing. However, creating a large number of strong hotspots remains challenging due to the difficulty in controlling the gap size to only a few nanometers. Recently, an elegant concept for manufacturing self-assembled nanofingers has been explored to tackle the aforementioned problems. Li et al. have successfully created ordered arrays of gold-capped-polymer nanofingers in a large area by nanoimprint lithography.[14] Controlled numbers of nanofingers can be readily snapped together by surface tension from solvent evaporation where hotspots were created in the junctions with an EF of ~$10^{11}$.[14a] [14b] However, nanoimprint lithography requires elaborate instruments and once the mask pattern is made, the arrangement of hotspots cannot be easily altered. Based on a similar concept, Schmidt et al. economically created hotspots in assembled silver-capped Si nanopillars via maskless reactive ion etching. At the most closely packed configuration of the nanopillars, a hotspot density of $30/\mu m^2$ and an EF $2.1\times10^{11}$ were achieved. However, the positions of the hotspots cannot be precisely controlled due to the irregular positioning of nanopillars.[15]

Example 1

Ordered Arrays of Raman Nanosensors for Ultrasensitive and Location Predictable Biochemical Detection The present inventors overcame the aforementioned problems by economically synthesizing SERS nanocapsules and flexibly assembling them into designed arrays with electric fields for ultrasensitive and location-predictable biochemical sensing. In one example, a plasmonic nanocapsule is taught having a tri-layer structure with a three-segment Ag/Ni/Ag nanorod as the core, a thin layer of silica as the capsulating layer, and uniformly distributed Ag NPs on silica as the hotspot layer (FIG. 1). Each layer in these nanocapsules serves a specific purpose. The inner metallic nanorod cores can be electrically polarized and thus manipulated by electric tweezers[16] based on combined AC and DC electric fields and the embedded Ni magnets in the nanorods assist the assembly of the nanocapsules onto patterned nanomagnets at designated locations; the central silica layer provides a supporting substrate for the synthesis of the Ag NP arrays, which also effectively separates the plasmonic Ag NPs from the metallic nanorod cores to eliminate plasmonic quenching; finally, the outermost layer made of Ag NPs with optimized sizes and junctions provides a large number of hot spots (~1200/$\mu m^2$) for ultrasensitive detection. The nanocapsules were transported and assembled into ordered arrays using nano-manipulation using the "electric tweezers". A 3×3 nanocapsule sensor array was made and it is demonstrated herein to successfully detect various biochemicals. Such Raman nanosensors are designed and fabricated to remove obstacles that hinder the applications of SERS and may permit new designs of Raman nanosensors.

Figure 2:
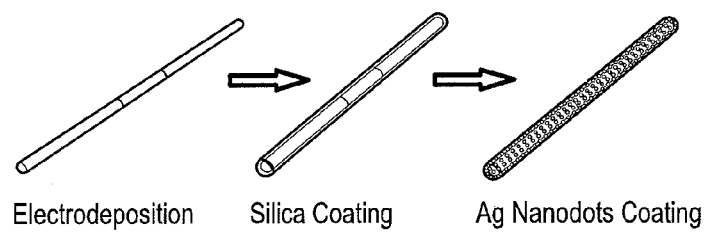
FIG. 2 shows one synthesis process of nanocapsules.

In one example, the fabrication of nanocapsules follows the steps in FIG. 2: first was the synthesis of multisegment Ag/Ni/Ag nanorods (300 nm in diameter, $L_{Ag}$=2.5 μm, $L_{Ni}$=1 μm) by electrodeposition in nanoporous anodized aluminum oxide membranes that have been described previously.[8c, 8d] In brief, a Cu layer of 500 nm in thickness was sputtered onto the back of the membrane to seal the pores and also serve as the working electrode in a three-electrode electrodeposition system. The electrodeposition of the nanowires from the working electrode commenced at the bottom of the nanopores. The amount of electric charge passing through the circuit controls the length of the segments of the Ag/Ni/Ag nanowires in the membrane. After dissolving the membrane in 2 M NaOH solution, the nanowires were washed by sonication and centrifuging in ethanol and deionized (D.I.) water twice before resuspended in D.I. water.

Figure 3A:
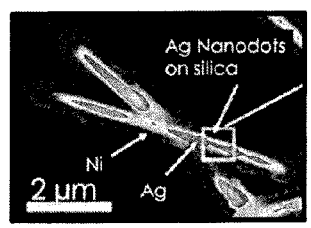
FIGS. 3A to 3F show color enhanced SEM images of tri-layer nanocapsules at (3A) low magnification and (3B) high magnification. (3C) The contrast enhanced image of (3B). (3D-3E) TEM images of a typical nanocapsule show a fairly uniform distribution of Ag NPs. (3F) Arrays of junctions of the Ag NPs<2 nm.
Figure 3B:
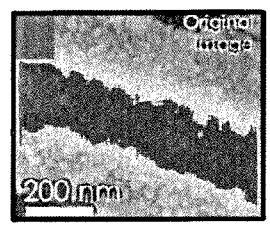

Next, the Ag/Ni/Ag nanorods were coated with 150 nm amorphous silica via hydrolysis of tetraethyl orthosilicate.[17] Here, the silica layers served as supporting substrates for synthesis of Ag nanodot arrays. Freshly prepared silver nitrate ($AgNO_3$, 0.06 M, 400 μl), ammonia ($NH_3 \cdot H_2O$, 0.12 M, 400 μl), and nanorods (5.7×10$^8$/ml, 400 μl) were mixed and stirred for 1 hour to let the silica adsorb adequate Ag ions before polyvinylpyrrolidone (PVP) (in ethanol, 10 ml of 2.5×10$^{-5}$ M) was added. The reactant mixture was incubated at 70° C. to allow PVP to reduce ionic Ag into metallic Ag NPs on silica. After the 7-hour reaction, arrays of Ag NPs were obtained on the surface of the nanorods as shown in FIGS. 3A and 3B. By varying the reaction conditions, the average particle size can be tuned from 8 nm to 25 nm as described next.

Optimization and characterization of the particle and junction sizes of Ag nanoparticles. The Ag NP sizes and junctions can be tuned and optimized by changing the ratio of $AgNO_3$ to ammonia. In the Ag NP coating step, 50 μl (1×), 200 μl (4×), 400 μl (8×), and 800 μl (16×) of $AgNO_3$ (0.06 M) were applied and ammonia (0.12 M) in four synthetic batches. The reactants were mixed and stirred for 1 hour before 10 ml polyvinylpyrrolidone (PVP) (in ethanol, 2.5×10$^{-5}$ M) was added. The resulting solution was incubated at 70° C. for 7 hours.

The morphologies of the as-synthesized Ag NPs differ in particle and junction sizes [FIG. 4A)]. The diameters of the Ag NPs were reduced from 20.8±5.7 nm (1× samples) to 17.6±6.0 nm (4× samples) to 8.2±6 nm (16× samples); however a diameter of 24.9±6 nm was found on the 8× samples.

The highest SERS enhancement was obtained from the 8× sample, which was selected and employed for SERS detection and E-field assembly in this research. FIG. 4B shows the SERS spectra of 1 μM of R6G adsorbed on nanocapsules (the incubation time was 2 hours and the nanocapsules were washed with ethanol) from the 1×, 4×, 8× and 16× samples. The 532 nm laser had a spot size of ~1 μm. The integration time was 1 second.

Figure 3C:
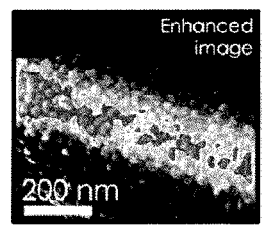
Figure 3D:
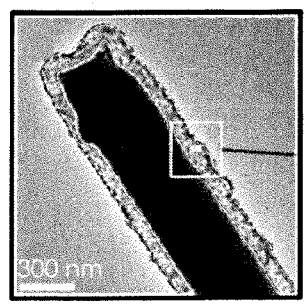
Figure 3E:
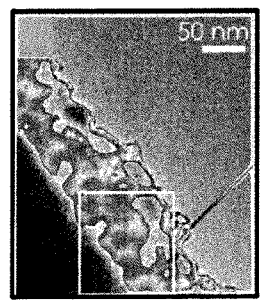
Figure 3F:
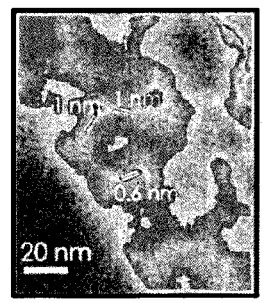

The highest enhancement of SERS was obtained from nanocapsules fabricated according to the conditions described above with a particle size of 25±6 nm as shown in the enhanced SEM image[18] in FIG. 3C. Such nanocapsules offer an estimated Ag NP density of 1600/$\mu m^2$. The junction sizes between the close neighboring NPs were analyzed with methods below for Particle and Junction Size Estimation. Looking at junctions of less than 2 nm between closely neighboring Ag NPs as hotspots, the E field is much stronger than that on the Ag NPs or in wider junctions (the hotspot density is estimated to be 1200/$\mu m^2$). TEM images evidenced large arrays of narrow junctions (<2 nm) in FIGS. 3D-3F.

Figure 6A:
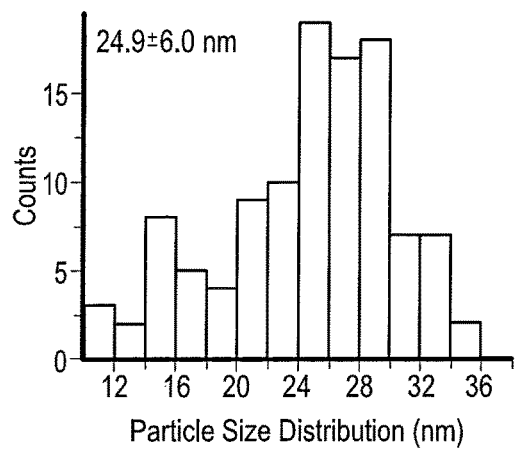

Particle and Junction Size Estimation. Measurement in the rectangular highlighted region of FIG. 5A shows the average diameter of the NPs was 24.9±6 nm. FIG. 5B shows an example of measurement of the diameters of nanoparticles from the enhanced SEM image. The size distribution of NPs is shown in the histograms in FIG. 6A. There were approximately 115 particles and 330 junctions in total in the measured region with an area of 0.07 $\mu m^2$ (0.16 μm×0.44 μm). Therefore the particle density is estimated to be 115/0.07 $\mu m^2$=1642/$\mu m^2$, and maximum junction density is estimated to be 330/0.07 $\mu m^2$=4714/$\mu m^2$. It was found that if the particles have uniform size and are close packed, each particle should have six neighboring particles, i.e. each particle contributes 3 junctions. In this ideal case, junction density is 1642/$\mu m^2$×3=4926/$\mu m^2$.

Figure 6B:
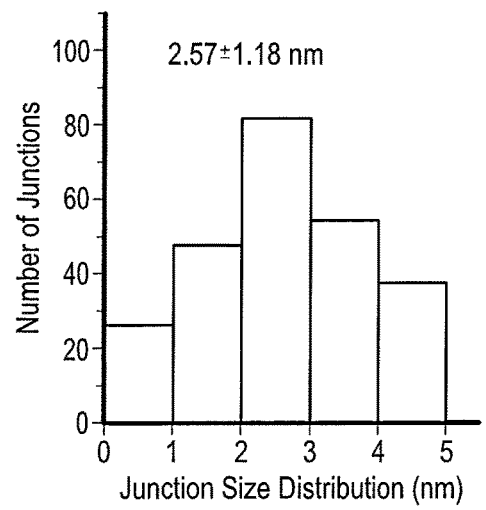
Figure 6C:
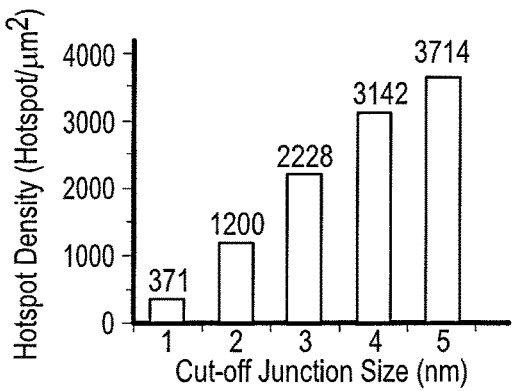

Next, the junction sizes between Ag NPs were directly measured. Because SERS enhancement drastically increases as junction size decreases and high EF of SERS is generally found in junctions of a few nanometers or less, only junctions≤5 nm were measured and noted that the measurement uncertainty can be large when the junctions have such small values due to the resolution limit of SEM. Also, it was assumed that the junctions have a size of 0.5 nm when NPs are too close to measure. With this method, (1) when only taking junctions of ≤5 nm as hotspots for SERS enhancement, a junction size of 2.57±1.18 nm was obtained and a hotspot/junction density of 3714/$\mu m^2$; (2) if assuming the hotspots are contributed from narrow junctions of ≤2 nm, a junction size of 1.17±0.5 nm was obtained and a hotspot/junction density of 1200/$\mu m^2$ as shown in the diagram of FIGS. 6B-6C.

Figure 7A:
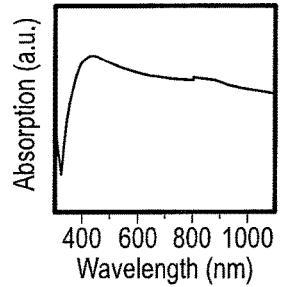
FIGS. 7A to 7G show the: (7A) Optical absorption of the tri-layer nanocapsules; (7B) SERS characterization of BPE from 1 pM to 1 $\mu$M shows clear SERS spectra; (7C) SERS intensity increases with BPE concentrations; (7D) Raman mapping profile of 1 $\mu$M R6G dispersed on a tri-layer nanocapsule shows uniform SERS intensity on the entire surface of the nanocapsules. (1655 $cm^{-1}$, scan step 250 nm, integration time 0.5 s) (7E) SERS intensity distribution along the nanocapsule. (7F) Variation of SERS spectra of R6G molecules in a 100-sec time frame with 1-sec integration for each spectrum. (7G) Intensity of SERS at 1655 $cm^{-1}$ as a function of time.
Figure 7B:
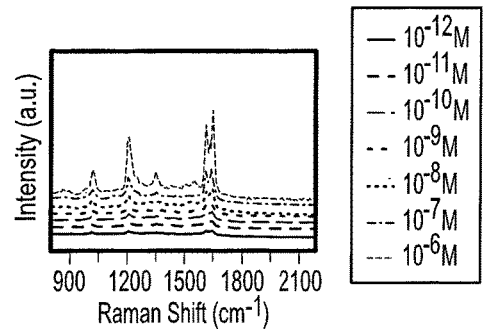
Figure 7C:
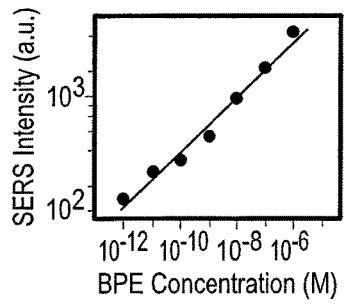

Before characterizing the SERS sensitivity of the nanocapsules, the optical absorption of the nanocapsules was studied to determine the optimal condition for SERS sensing. Here the Ag/Ni/Ag metal-cores were removed with the understanding that most excitation light was absorbed by the outermost Ag nanodot layers while little energy actually goes to the metal cores. The nanocapsules exhibited an absorption peak at 450 nm due to the collective plasmonic resonance of assembled Ag NPs [FIG. 7A]:[19] Since the absorption was very sensitive to both the size and geometry of nanoparticles, it showed a broad background due to the size and shape distribution of the Ag NPs. With available lasers from 532-633 nm, a 532 nm laser (random polarized) was chosen as the excitation source for Raman scattering measurement because the wavelength of 532 nm is closer to the absorption peak and laser energy can be more effectively absorbed by the nanocapsules, which results in high intensity E-field focused at the hot spots and thus high EF for SERS detection. Indeed, the nanocapsules detected Raman spectra of 1,2-bi-(4-pyridyl)ethylene (BPE) with a concentration as low as $10^{-12}$M (1 pM) [FIG. 7B]. The intensity of the SERS at 1644 cm$^{-1}$ logarithmically increased with the concentration of BPE from 1 pM to 1 μM as shown in FIG. 7C. The details are described next.

Details of the concentration dependent SERS detection and SERS Mapping. (a) Concentration dependent SERS detection: Nanocapsules were sparsely dispersed in a 3 mm-diameter well made of 1 mm-thick Polydimethylsiloxane (PDMS) film. BPE (10 μl in ethanol) with concentrations from 1 pM ($10^{-12}$ M) to 1 μM ($10^{-6}$ M) added to the PDMS well and sealed with a cover slip. The nanocapsules were incubated in BPE solution for 10 minutes. before being rinsed with ethanol three times for SERS detection. A 532 nm laser was used for Raman excitation. Each SERS spectrum was collected from a single focusing spot (~1 μm) on a nanocapsule and integrated for 5 seconds at the same conditions.

(b) SERS mapping: The functionalization of R6G on nanocapsules follows a procedure that is often used in R6G SERS sensing:[22g] Nanocapsules were dispersed on a glass substrate and dried in air. The nanocapsules were then incubated in 1 μM R6G ethanol solution for 2 hours before being washed with ethanol and dried. The Raman mapping was conducted on a single nanocapsule by using a confocal 532 nm Raman microscope. The laser spot size was approximately 1 μm, scanning step was 250 nm, and integration time was 0.5 second.

The SERS EF of the nanocapsules was further evaluated. The EF of the nanocapsules was measured and estimated to be $1.1 \times 10^{10}$ following a widely used method[14a, 15] as described next.

SERS Enhancement Factor Estimation. The SERS EF was calculated by following an commonly used method reported elsewhere[14a, 15] as given below:

$$EF = \frac{I_{SERS}/N_{SERS}}{I_{RS}/N_{RS}}, \quad \text{Eq. S1}$$

$N_{SERS}$ is the average number of adsorbed molecules enhanced by SERS substrate in the detection volume, $I_{SERS}$ is the corresponding SERS intensity, $N_{RS}$ is the average number of molecules excited without surface enhancement, and $I_{RS}$ is its corresponding Raman intensity.

The values of $I_{RS}$ were obtained from 0.1 M BPE in ethanol. A low laser power of 35 μW (532 nm) was chosen to avoid intensity saturation as well as photo-degradation of the analyte. The laser was fully focused into the BPE solution via a 50× objective. A Raman spectrum with an intensity ($I_{RS}$) of 0.5 counts/second (at 1200 cm$^{-1}$) was obtained.

$N_{RS}$ is given by $N_{RS}=V_{scat} C_{BPE} N_A$, where $V_{scat}$ is the scattering volume of BPE that contributes to the measured Raman signal, $C_{BPE}$ is the concentration of the BPE (0.1 M), and $N_A$ is Avogadro's number. $V_{scat}$ is given by $V_{scat}=A_{obj}H_{obj}$, where $A_{obj}=\pi (0.5$ μm$)^2$ is the area of the laser spot from the 50× objective and $H_{obj}$ is the effective height of the detection volume of BPE. Therefore, $N_{RS}=A_{obj}H_{obj}C_{BPE}N_A$. The $H_{obj}$ was determined by using the method reported elsewhere:[25] In brief, the measurement was carried out by moving a silicon <100> wafer with 1 μm increment through the focal plane of the objective and collecting the intensity of Si Raman signal at 520 cm$^{-1}$ at each point. $H_{obj}$=13 μm was obtained by integrating the intensity of Raman signal with distance and then dividing by the highest measured signal. By using this method, $V_{scat}$ was determined to be 10.2 μm$^3$.

Therefore, the total number of molecules ($N_{RS}$) can be readily known:

$$N_{RS}=0.1 \text{ mol/L} \times 10.2 \text{ μm}^3 \times 6.02 \times 10^{23} \text{molecules/mol}=6.14 \times 10^8 \text{ molecules}.$$

To determine the value of $I_{SERS}$, nanocapsules were dispersed on a glass substrate and dried them in air, and then incubated them in 1 mM BPE in ethanol for 10 minutes. The nanocapsules were then rinsed with pure ethanol to remove excess molecules and dried in air. Since the nanocapsules are cylinders with curvature (600 nm in diameter), the effective area excited by the laser (spot size 1 μm) was approximated to be 1 μm×0.2 μm=0.2 μm$^2$. Under the same experimental condition as described above, an $I_{SERS}$ of 20000 counts/second (at 1200 cm$^{-1}$) was obtained. Assuming that molecules residing in the 1.6 nm$^3$ volume of the 1.17±0.5 nm narrow junction contribute the most to the measured Raman intensity (the junction size was), where there were approximately 9 molecules/junction for a close packed monolayer of BPE (3 Å×6 Å×10 Å/molecule),[14a] provides $$N_{SERS}=0.2 \text{ μm}^2 \times 1200 \text{ hotspots/μm}^2 \times 9 \text{ molecules/hotspot}=2160 \text{ molecules}$$

Therefore, $$EF = \frac{I_{SERS}/N_{SERS}}{I_{RS}/N_{RS}}$$
$$= \frac{20000/2160}{0.5/(6.14 \times 10^8)}$$
$$= 1.1 \times 10^{10}.$$

Figure 7D:
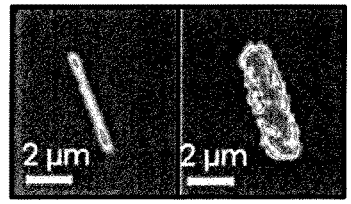
Figure 7E:
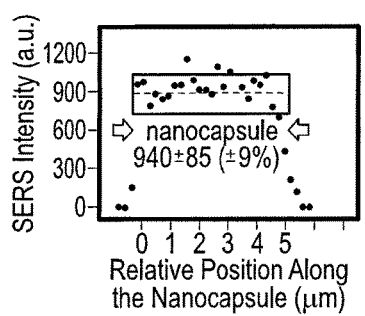
Figure 7F:
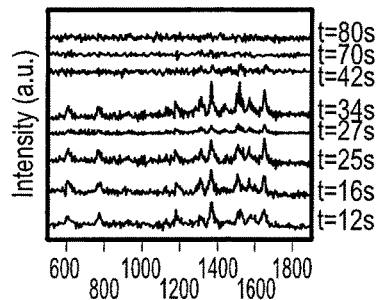
Figure 7G:
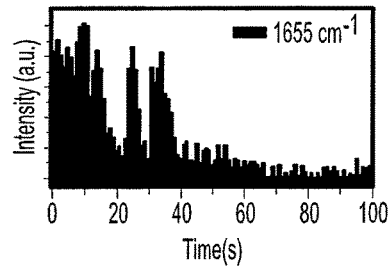

According to the bi-analyte and temperature-dependent SERS vibrational pumping methods, an EF of the order of $10^7$-$10^8$ is sufficient for detection of single molecules of various analytes.[20] A SERS substrate with EF of $5 \times 10^9$ has detected a single BPE molecule.[21] Therefore, the high EF value found in the nanocapsules suggests their single-molecule sensitivity. Moreover, the inventors observed both a strong intensity and frequency fluctuation of Raman spectra from extremely low-concentration R6G (1 pM), which are consistent with single-molecule behaviors attributed to molecular diffusion into and out of hotspots [FIGS. 7F-7G and details of detection of Raman fluctuation, next], according to previous reports.[7, 22] As a result, the SERS characterizations have placed the sensitivity of the nanocapsules in the single molecule regime, even though they are not absolute proofs.[22a]

Details of detection of Raman fluctuation. Nanocapsules were dispersed on a glass substrate and dried in air. They were then incubated in 1 pM R6G for 2 hours before being rinsed with pure ethanol and dried. SERS characterization was carried out with a 50× objective and the 532 nm laser power was 35 μW. SERS spectra were recorded with an integration time of 1 second for 100 seconds.

Raman mapping of R6G shows that SERS enhancement was fairly uniform on the nanocapsules. At a concentration of 1 μM, R6G forms a monolayer on the nanocapsules (described hereinabove). Different colors in the Raman mapping represent different Raman intensities of R6G. The Raman intensity at 1655 cm$^{-1}$ was essentially uniform along the axis of the nanocapsules and reduced to zero towards the edges of the nanocapsules due to the deflated laser on the edges [FIG. 7D]. Analysis along the nanocapsules shows that the variation of the Raman intensity (at 1655 cm$^{-1}$) is within ±9% [FIG. 7E]. This low variation suggests that the nanocapsules can readily detect monolayer analyte with good repeatability and predictability over their entire surface. Note that the tolerance of detection is actually less than ±9% since the coverage of R6G on nanocapsules cannot be absolutely uniform. Two factors determine this uniformity: (1) the controlled sizes and spacing of the Ag NPs, which gives relatively low variation of EF among hotspots; (2) the large number of hotspots of around 240 in each detection area [1200/μm$^2$ (hot spot density)×0.2 μm (⅓ of nanocapsule diameter due to nanocapsule curvature)×1 μm (laser spot size)]. As a result, the SERS effect is uniform along the nanocapsules because of the averaged EF from all the hotspots in each detection position. It was further note that the uniform SERS detection demonstrated on the nanocapsules is for monolayer chemicals. With reduced concentration of the analyte (less than that of a monolayer), the larger variation of SERS along the nanocapsules should be expected and the ultimate tolerance is determined by the difference of EF from individual hotspots on the entire nanocapsules.

Different from most previous reports of SERS sensing nanostructures, the Raman nanocapsule sensors of the present invention are designed for facile assembly at designated locations. Previously, seek-and-find efforts are generally required for SERS sensing devices due to the randomness of hot-spots. The difficulties of prior efforts greatly hindered the development of SERS for realistic applications. It is highly desirable to assemble the hot-spots at designated locations for location-predictable biosensing. Previously, substantial efforts were carried out to tackle such a problem;[11-13] however, it remains a daunting task to obtain Raman sensors with reliable spatial accuracy. Here, a strategical design of the nanocapsules is presented that facilitates the rational assembly of hot-spots for location-predictable Raman sensing by using electric tweezers, using the present inventors' contactless nanomanipulation technique.

Electric tweezers is based on combined DC and AC electric fields for precision orientation and transport of metallic nanowires in aqueous suspension, the fundamentals of which have been reported elsewhere[16a, 16c-f, 23] In brief, in a combined DC and AC electric (E) field, a longitudinal nanoparticle can be transported by the DC E field due to electrophoretic force and aligned by the AC E field due to dielectrophoretic force. The transport and alignment can be controlled completely independently by the DC and AC E fields, respectively. Applying the combined E fields in both X and Y directions with controlled duration, longitudinal nanoparticles such as nanowires can be readily transported along prescribed trajectories on a 2-D surface with a precision of at least 150 nm[14a, 14d].

Figure 8A:
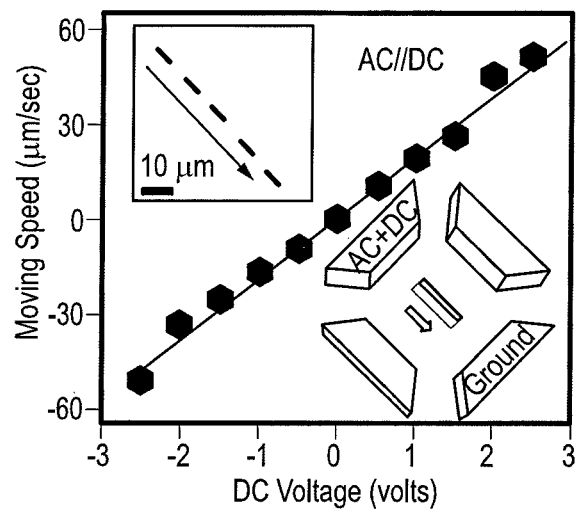
FIGS. 8A to 8B show the AC and DC configurations on quadruple electrodes for the manipulation of nanocapsules. The nanocapsules are aligned in the direction of AC E field and transported in the direction of the DC E field. Nanocapsules were transported with controlled speed and orientation using "electric tweezers", (8A) parallel (AC//DC) and (8B) perpendicular (AC⊥DC) to their own alignment directions as shown in the overlapped optical images. Transporting speed is linearly proportional to the applied DC voltage.
Figure 8B:
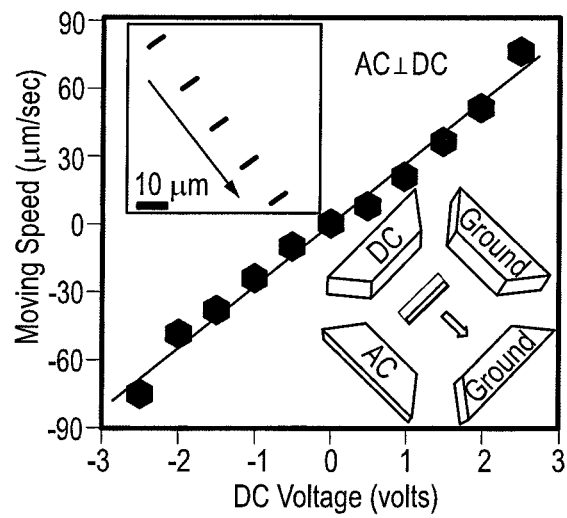

In this work, the electric-tweezers manipulation technique was leveraged with the unique magnetic Ni embedment in the Ag/Ni/Ag core of the nanocapsules to assemble an ordered plasmonic nanosensor array on prepatterned nanomagnets as shown in FIG. 9. Uniform AC and DC E fields were established in a quadruple microelectrode chip with two pairs of parallel-electrodes separated at a distance of 500 μm. At the center of the quadruple microelectrode, a 3×3 nanomagnet array was fabricated through standard e-beam lithography [FIG. 10A]. Each nanomagnet with diameter of 1 μm actually includes of a trilayer structure: 6 nm Cr adhesion layer on the substrate, 100 nm Ni layer providing magnetic fields, and 100 nm Au layer for tuning the magnetic interaction force. Nanocapsules suspended in D.I. water were dispersed at the center of the quadruple electrodes. The nanocapsules can be readily transported parallel [FIG. 8A, AC//DC] or perpendicular to their orientations [FIG. 8B, AC⊥DC], similar to earlier manipulation of Au nanowires[6a, 16d, 16e], by applying electric tweezers with a combined AC (15V, 20 MHz) and DC voltages (−2.5V to +2.5V) on the quadruple electrodes. The transporting speed linearly increased with the applied DC voltages for both orientations and reached approximately 80 μm/second at 2.5 V in vertical transport. It was found that the Ag/Ni/Ag nanorod cores in the nanocapsules played a critical role in steering the transport orientations. After their metallic cores had been etched away,[24] the hollow nanotubes were transported by a DC E field; however, the orientations of the nanotubes were uncontrollable by AC E field due to the weak polarization and low alignment torques of insulating silica nanotubes in an AC E field (FIG. 11). Therefore, the metallic Ag/Ni/Ag rod was useful for positioning the Raman nanosensors in order to facilitate steering of the orientation.

After the nanocapsules were successfully transported in the microelectrodes, the next task was to assemble them on arrays of nanomagnets for location predictable SERS sensing. By programming the AC and DC E fields in both X and Y direction, the nanocapsules were moved along a prescribed trajectory, such as "steps", with orientations either parallel [FIG. 10B] or perpendicular [FIG. 10C] to their transport directions. When nanocapsules were maneuvered into the vicinity of nanomagnets by the electric tweezers, the magnetic attraction force securely anchored the nanocapsules on the top of the nanomagnets. The magnetic force was between the nickel segments in the core of the nanocapsules and the Ni layer in the patterned nanomagnets on the chip. The manipulation of the nanocapsules was so versatile and precise that a nanocapsule was easily maneuvered to pass by a few neighboring nanomagnets and anchored it on a nanomagnet at the center of the array and other locations [FIGS. 10D and 10E]. In this manner, an array of nanocapsules was assembled on top of nanomagnets as shown in FIG. 10F, where the bright circles indicate nanomagnets. A representative video clip of the assembling process is provided in the supporting information. Finally, from the assembled nanocapsule arrays, the present invention was used to successfully detected SERS of various chemicals including R6G, methyl blue and BPE and realized location predictable biochemical sensing by design as shown in FIG. 10G. Note that the probability of single-molecule detection increases with the number of hot-spots on the nanocapsules excited by the laser. This can be readily achieved by increasing the size of the laser spot, having prescribed scanning along the nanocapsules, and even by trapping multiple nanocapsules on a single nanomagnet.

In summary, the present inventors rationally designed and fabricated a new type of nanocapsule SERS sensor to tackle the two great obstacles in the development of SERS technology: (1) the lack of a large quantity of hotspots with controlled gaps; (2) the difficulty of assembling SERS probes at designated locations. These nanocapsule sensors have of three functional layers. The outer sensing layers, made of large numbers of plasmonic NPs with controlled size and gaps, offer ultrasensitive SERS detection on the entire surface of the nanocapsules. The central silica-coating layer provides support for the outer sensing layers and eliminates the plasmonic quenching effect. In certain aspects, the inner metallic Ag/Ni/Ag core is the key component for steering the orientation of nanocapsules during manipulation by the electric tweezers. With electric tweezers, the nanocapsules were transported and anchored on patterned nanomagnet arrays due to the magnetic attraction between the Ni segment within nanocapsules and the patterned nanomagnets. As a result, an ordered array of Raman nanosensors has been rationally designed and fabricated for application in ultrasensitive and position-predictable SERS detections. The design and fabrication of nanocapsules provides new devices for the development of new types of Raman nanosensors to realize the full potential of SERS effect.

Example 2

Near-field enhanced bifunctional plasmonic-magnetic (PM) nanostructures consisting of silica nanotubes with embedded solid nanomagnets and uniformly dual-surface-coated plasmonic Ag nanoparticles (NPs) are rationally synthesized. The solid embedded sections of nanotubes provide single-molecule sensitivity with an enhancement factor up to $7.2\times10^9$ for Surface-Enhanced Raman scattering (SERS). More than 2×SERS enhancement was observed from the hollow section than the solid section of the same nanotube. The substantial SERS enhancement on the hollow section is attributed to the dual-sided coating of Ag NPs as well as the near-field optical coupling of Ag NPs across the nanotube walls. Experimentation and modeling were carried out to understand the dependence of SERS enhancement on the NP sizes, junctions, and the near field effects. By tuning the aspect ratio of the embedded nanomagnets, the magnetic anisotropy of nanotubes can be readily controlled to be parallel or vertical to the long directions for nano-manipulation. Leveraging the bifunctionality, the present inventors magnetically maneuvered such a nanotube to a single living mammalian cell amidst many and analyzed its membrane composition via SERS spectroscopy.

Bifunctional plasmonic-magnetic nanoparticles (PM-NPs) are unique hybrid nanomaterials that include both optical and magnetic components in a rationally-designed nanoscale architecture and have recently attracted intense research interest.[1] Possessing both enhanced optical and magnetic properties, PM-NPs can be extremely useful for biomedical applications that require either optical sensing/imaging/heating, magnetic stimulation/manipulation, or both functionalities.[1a, 1b, 1d, 2] For instance, PM-NPs can attach to biological entities such as cells and molecules to separate those entities under external magnetic fields and simultaneously detect their chemical nature via optical sensing.[3] The PM-NPs can also be deployed to study the mechanical properties of deeply embedded biological tissues by magnetic field-induced mechanical stimulation[4] and monitoring the responses by in-situ optical imaging.[5] However, current available bifunctional PM nanostructures have been largely limited to quasi-zero-dimensional (0-D) nanostructures, such as nanospheres and nanoshells.[1a-d, 2a] To the inventors' knowledge, there are few reports on quasi-one-dimensional (1-D) PM nanostructures, although 1-D PM nanostructures provide exclusive advantages for biomedical applications that are unavailable for 0-D nanostructures.

In this EXAMPLE 2, a unique type of 1-D PM nanotubes is shown and used for targeted, single-cell sensing. The PM nanotubes consist of silica nanotubes with embedded solid Ni nanomagnets and uniformly dual-surface-distributed plasmonic Ag NPs. The PM nanotubes provide a high hotspot density (approximately $1200/\mu m^2$ on the outer surface) at the junctions of Ag NPs for SERS biodetection. The solid embedded sections of nanotubes provide single-molecule sensitivity with an enhancement factor up to $7.2\times10^9$. More than 2× SERS enhancement was observed from the hollow sections than that from the solid section of the same nanotube. This substantial SERS enhancement is induced by the double-sided coating of Ag NPs on the nanotubes as well as the near-field optical coupling between Ag NPs on the inner and outer surfaces of the nanotubes. The dependence of SERS enhancement on the particle sizes, junctions, and the near field effects was carried out by both experimentation and modeling. The magnetic anisotropy of the nanotubes, due to the embedded nanomagnets, can be readily tuned to be parallel or vertical to the long direction of the nanotubes for controlled manipulation. Leveraging the nanotubes' unique bifunctionality, a nanotube was magnetically maneuvered to a living Chinese Hamster Ovary cell and detected the membrane composition of the specific cell with SERS spectroscopy. These bifunctional nanotubes are desirable for multiple-task applications in single-cell bioanalysis, biochemical detection, imaging-contrast enhancement, magnetic manipulation and separation, and biosubstance or active agent delivery.

There are three outstanding features provided by the 1-D PM nanotubes: First, the unique longitudinal geometry of nanotubes is compatible with both biological cells and biomolecules in terms of length and diameter. For instance, the lengths of nanotubes can be adjusted to tens of micrometers for efficient attachment, manipulation, and separation of cells.[6] The nanoscale diameters restrict the number of molecules that one nanotube can interact with, which is important for molecule-level biosensing and drug delivery.[7] Second, substantially enhanced plasmonic properties are sensitively obtained in the nanotubes. The plasmonic NPs coated on the entire surfaces of the nanotubes provide large and uniform SERS EFs, similar to those frequently reported in patterned substrates,[8] which are provided by traditional 0-D plasmonic NPs or their aggregates. Third, by controlling the aspect ratio of the embedded Ni nanosegment, the magnetic moment and anisotropy can be facilely tuned to the desired value, which is important for efficient magnetic separation and manipulation.[9]

Figure 13A:
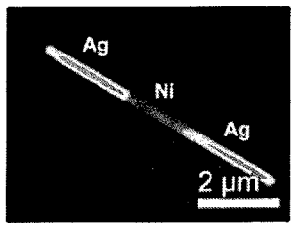
FIGS. 13A to 13F show: Scanning Electron Microscopy images of (13A) multi segment Ag/Ni/Ag nanowires, (13B) silica nanotubes embedded with Ni nanomagnets, (13C) silica nanotubes with high-aspect-ratio Ni segments and surface-coated Ag NPs, (13D) low-aspect-ratio Ni segments in the nanotubes, (13E) close view of the Ag NPs on nanotube surface (13F) cross-sectional images of nanotubes obtained by FIB milling show the nanotubes are hollow with Ag NPs on both the inner and outer surfaces.
Figure 13B:
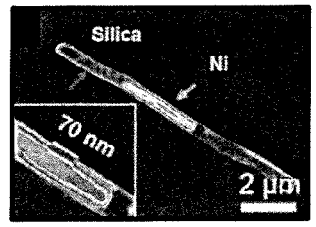

PM Nanotube Design and fabrication: In order to synthesize such PM nanotubes, a rationally designed four-step approach has been used: (1) multi-segment Ag/Ni/Ag (3/3/3 μm) nanowires were electrodeposited as growth templates for silica nanotubes (FIG. 12A & FIG. 13A); (2) a layer of silica, with controlled thickness of 70 nm, was uniformly plated on the outer surface of the Ag/Ni/Ag nanowires (FIG. 12B) via hydrolysis of tetraethyl orthosilicate[10]; (3) the Ag segments were selectively etched, resulting in the hollow silica nanotubes with magnetic Ni embedment (FIG. 12C & FIG. 13B); (4) Plasmonic Ag NPs were uniformly coated through PVP assisted catalysis[11] on the inner and outer surfaces of the nanotubes with optimized particles and junction sizes (FIG. 12D & FIGS. 13C & 13E).

Figure 13C:
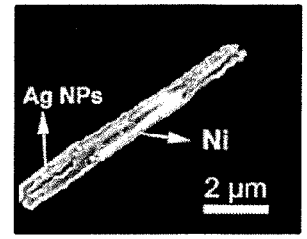
Figure 13D:
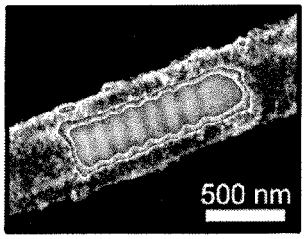
Figure 13E:
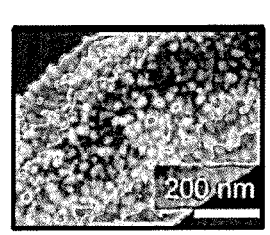
Figure 13F:
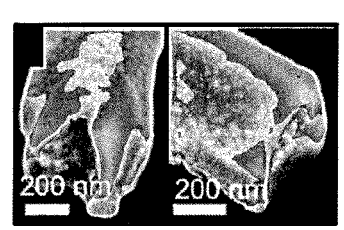
Figure 14A:
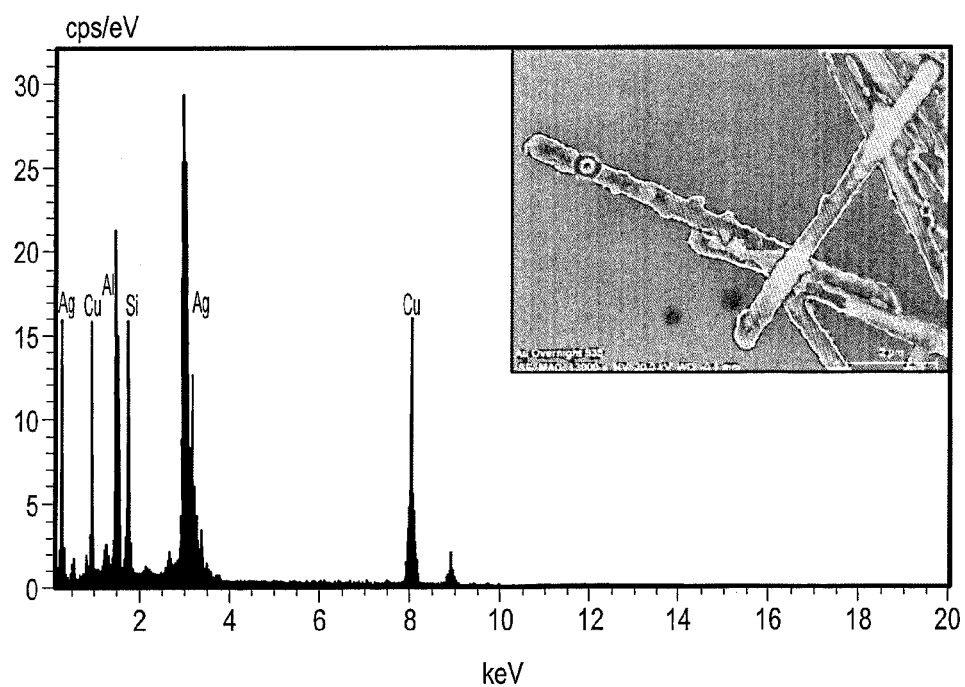
FIG. 14A shows the ends of the nanotubes made with Ag and silica and FIG. 14B shows EDS shows the center part of nanotubes made with Ni, Ag and silica.
Figure 14B:
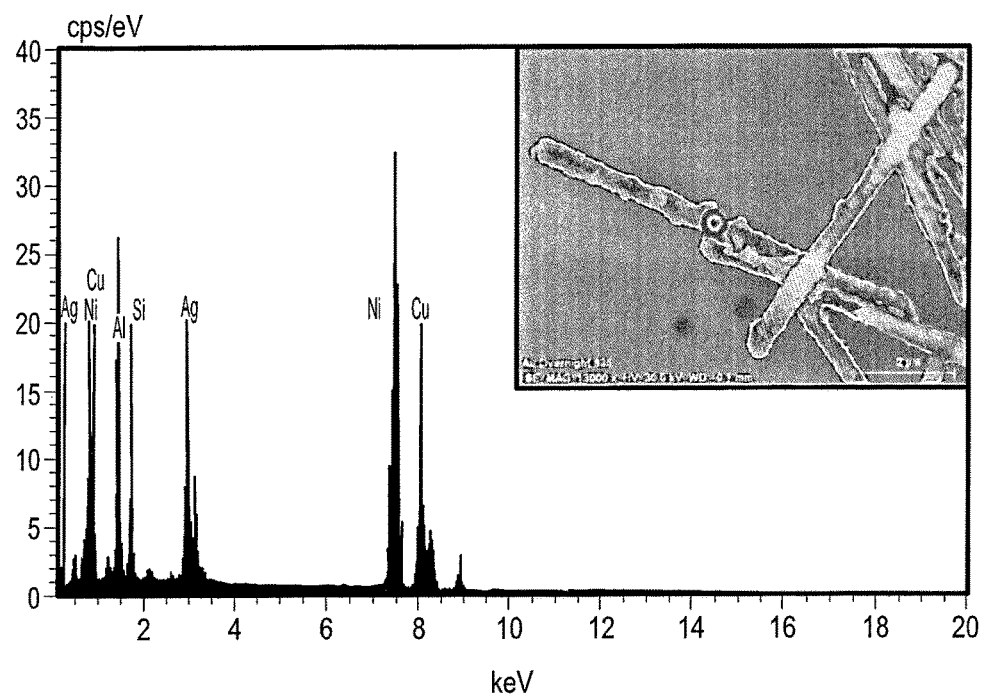

Scanning Electron Microscopy (SEM) images show that hollow nanotubes with embedded cylindrical solid segments were successfully synthesized (FIG. 13C). Energy Dispersive X-Ray Spectroscopy (EDS) confirmed that the cylindrical solid was Ni (FIGS. 14A and 14B show energy dispersive X-Ray spectroscopy of Ni embedded nanostructures (Al and Cu peaks are from the substrate). By using the same method, multiple Ni nanodisks with controlled magnetic anisotropies (thickness of 30 nm) can be readily embedded in the nanotubes (FIG. 13D). On the entire outer surface of nanotubes, arrays of Ag NPs were uniformly distributed (FIG. 13E). The Ag NPs also grew on the interior surfaces of the nanotubes as shown in the SEM images obtained by cross-sectional Focused Ion Beam (FIB) milling (FIG. 13F). The Ag NPs were semi-spherical and densely arranged, yet overlapping NPs were rarely found.

Figure 15:
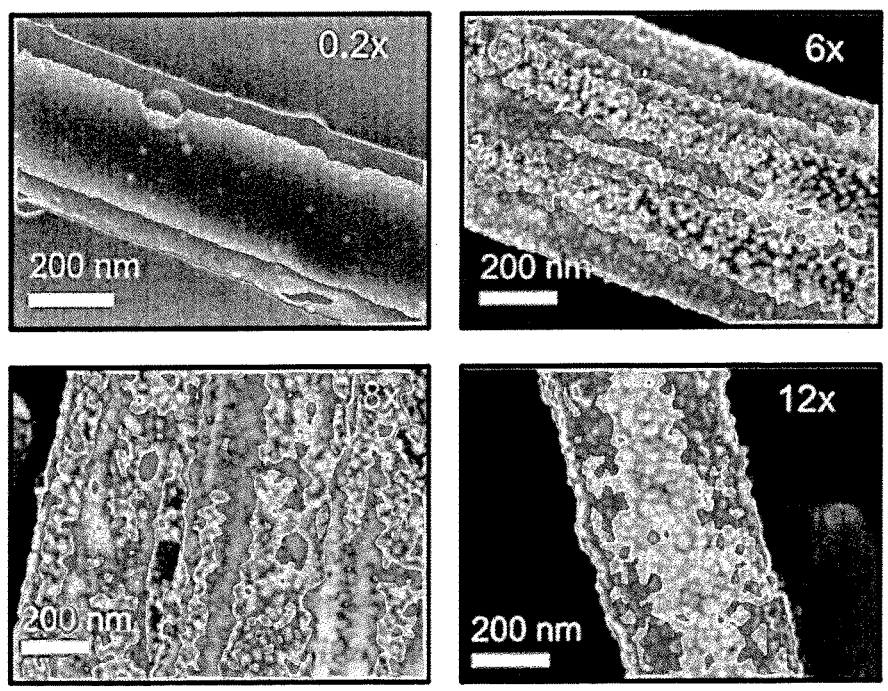
FIG. 15 SEM images of samples fabricated at different conditions. Sample 0.2×, 0.6×, 0.8×, 12×.
Figure 16:
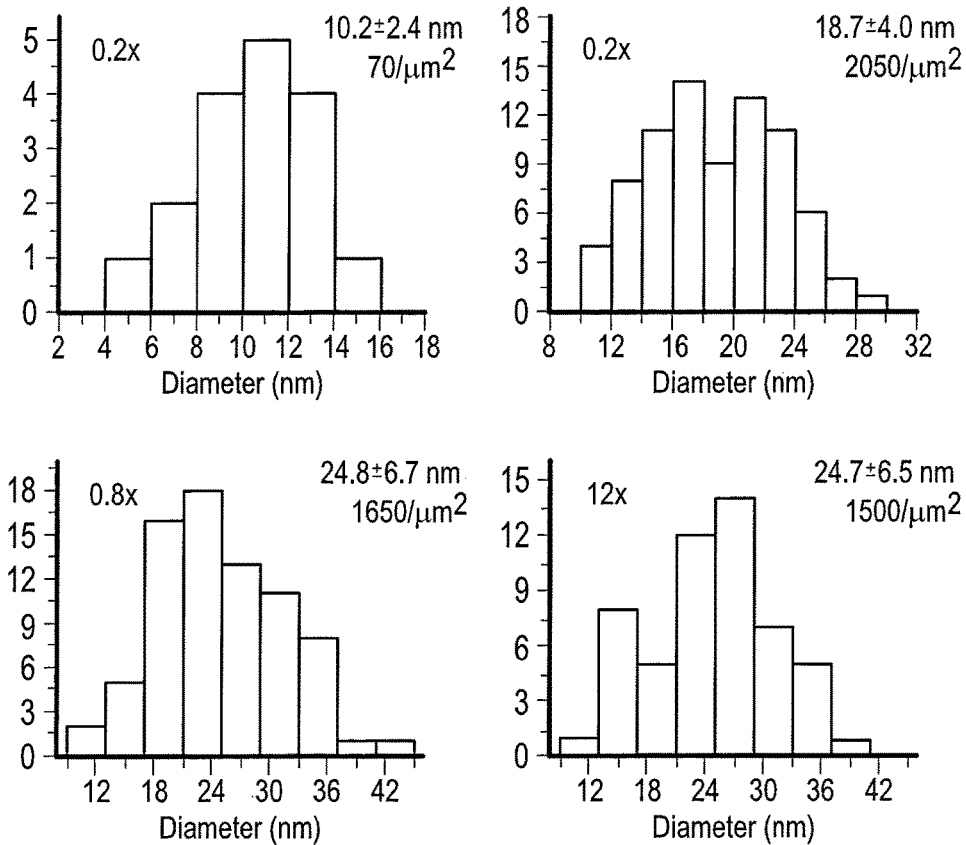
FIG. 16 shows the particle size and density distribution of Ag NPs of different samples. Sample 0.2×, 0.6×, 0.8×, 12×.
Figure 17:
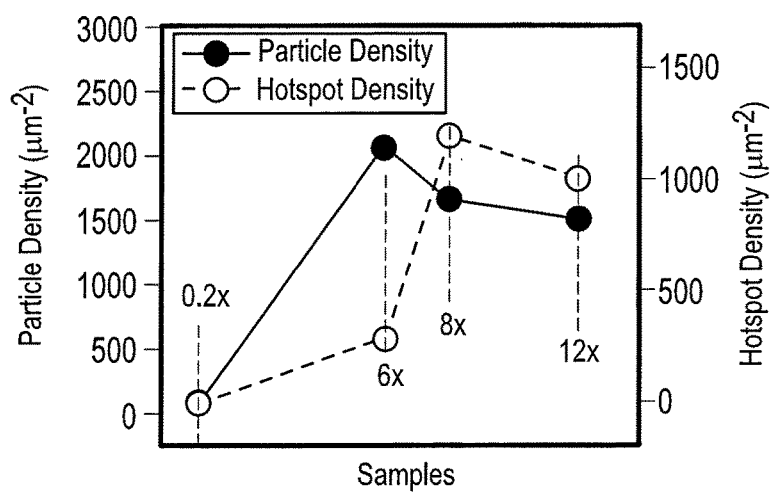
FIG. 17 shows the particle density and hotspot/junction density (<2 nm) of different samples. Sample 0.2× to sample 12×.

The Ag NP sizes and junctions can be optimized for highly sensitive SERS detection. With fixed volume of nanowire suspension ($5.7 \times 10^8$/ml, 400 μl) and PVP (10 ml of $2.5 \times 10^{-5}$ M in ethanol), the total volume of $AgNO_3$ was systematically varied (0.06M) and $NH_3 \cdot H_2O$ (0.12 M) (v:v 1:1) from 20 μl to 1200 μl, i.e. 20 μl (0.2× sample), 600 μl (6× sample), 800 μl (8× sample), and 1200 μl (12× sample). The morphologies of the as-synthesized nanotubes showed distinctive particle and junction sizes (FIG. 15). The average diameters of the Ag NPs increased from 10.2±2.4 nm (0.2× sample) to 24.8±6.7 nm (8× sample) with the volume of the $AgNO_3/NH_3 \cdot H_2O$ solution. The density of Ag NPs reached a maximum in the 6× sample (2050/μm$^2$). The detailed characterization is given in FIG. 16, FIG. 17, and Table 3. The variation of the particle sizes may be attributed to the dynamic competition between nucleation and crystalline growth of Ag NPs, which has been commonly observed in NP growth[12].

SERS characterization: The SERS performance of the nanotubes were characterized and understood by experimentation and numerical simulation. It is known that a laser-beam focused on two closely neighboring Ag NPs can generate high-intensity electric (E) field in the narrow junction (a few nm) due to localized surface plasmonic resonance as a result of coherent electron oscillation in the Ag NPs. The junction with enhanced E-field is often referred as "hotspot". If a molecule is in the vicinity of a hotspot, its Raman scattering signals can be significantly amplified with $|E|^4$ dependence. This phenomenon is the so-called Surface Enhanced Raman Scattering (SERS).[13] SERS EF is largely determined by E-field intensity and thus the sizes of junctions. If only extremely narrow junctions (<2 nm) on the nanotubes were consider, which contribute most to SERS enhancement, the density of hotspots on the outer surface of nanotubes went up from ~0/μm$^2$ for the 0.2× sample to the maximum of 1200/μm$^2$ for the 8× sample (see Estimation of SERS enhancement factor, below). The corresponding average hotspot sizes can also be determined. The 8× samples provided the smallest average size of hotspots (1.16 nm) and the 6× sample gave the largest (1.4 nm) as shown in FIG. 18D and described in Estimation of SERS enhancement factor.

Setup and procedure of SERS characterization. A Raman microscope equipped with a high precision motorized stage (resolution: 50 nm) was used for SERS characterization. A 532 nm laser was employed as the Raman excitation source. In the Raman testing, the nanotube samples were first dispersed on a glass slide, dried and incubated them in 1 mM BPE (ethanol solution) for 10 min, before rinsed them with pure ethanol to remove excess molecules.

Plasmonic simulation. It is interesting to understand how the EF depends on Ag particle and junction sizes, as well as how the Ag NPs on the hollow structures can further enhance SERS. Numerical simulation was conducted for such a purpose. Only the nanotubes fabricated in the same batch (300 nm in inner diameter and 70 nm in shell thickness) were compared.

To understand how the dual-side-Ag-coated hollow nanotubes can further enhance SERS than the single-side-Ag-coated nanotubes with solid embedment do, numerical simulations by Comsol 3.5a RF module were carried out. In this modeling, a three-dimensional (3-D) silica nanotube is constructed (illustrated in FIG. 12D & inserts): the inner cylinder radius is 150 nm, and the shell thickness is 70 nm. The densely coated Ag NPs are simplified by a 2-D conformal array attached to the outer and inner surfaces of the silica nanotubes. The Ag NP diameter is 25 nm and the gap between them is 2 nm. The silica nanotube is placed on top of a glass substrate, and is excited by a surface normal Gaussian beam with beam diameter of 1 μm at 532 nm wavelength. The polarization direction is perpendicular to the axis of the cylinder. Table 1 lists the simulation results corresponding to the measured devices and FIGS. 18A to 18D show the cross sectional views of the electric field distribution of the four devices as listed in Table 1.

TABLE 1

Simulation parameters for plasmonic magnetic nanotubes. (D is particle size).

| | Outer layer | Inner layer | Ag NPs |
| --- | --- | --- | --- |
| Simulation 1 | Ag NPs | Hollow (air) | D = 25 nm, gap = 2 nm |
| Simulation 2 | Ag NPs | Ag NPs | D = 25 nm, gap = 2 nm |
| Simulation 3 | Ag NPs | Pt | D = 25 nm, gap = 2 nm |
| Simulation 4 | Ag NPs | Ni | D = 25 nm, gap = 2 nm |

Figure 18A:
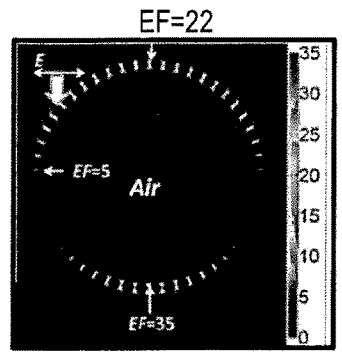
FIGS. 18A to 18D show simulation results show the cross sectional views of the optical induced electric field enhancement of the four devices as listed in Table 1.
Figure 18B:
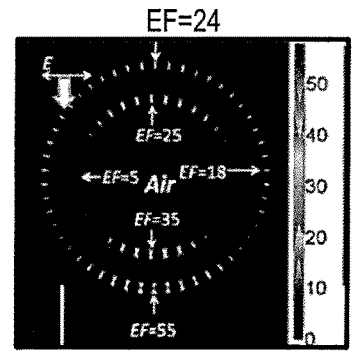
Figure 18C:
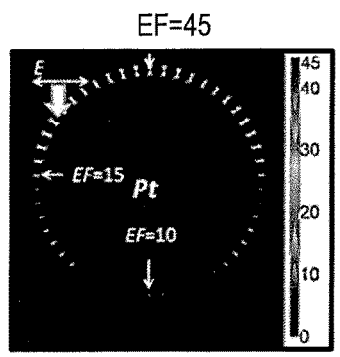
Figure 18D:
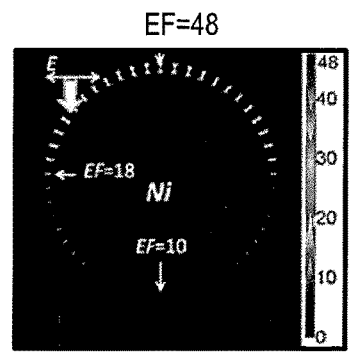

In FIG. 18A, surprisingly, it was found that the hot-spot with maximum electric field enhancement is actually at the bottom of the nanotube, not at the top. This is because the bottom hot-spot is surrounded by high-index silica; while the other hot-spots have only one side contacted with silica (other side is exposed to low-index air). Additionally, the inter-particle coupling through the NP chain at the outer surface enhances the electric field at the bottom[17]. Comparing FIGS. 18A-18B, it is possible to conclude that the contribution of inner layer Ag NPs: the presence of inner layer not only adds more hot spots for SERS sensing, but also significantly increase the intensity of the hot spots in the outer layer NPs, which is due to the near-field effect[18] of inter-layer coupling between NP chains in the inner and outer surfaces of the nanotubes. When the air core is filled with Pt, which has no surface plasmonic resonance at visible wavelength, interesting and unexpected phenomena were observed: first, the EF of the hot-spots on top of the nanotube is enhanced roughly 2×, which is due to the reflected light from the Pt core; second, the hot-spots at the bottom of the nanotube, however, is significantly reduced because almost no light can penetrate the Pt core to excite the surface plasmons. Moreover, the inter-particle coupling through the NP chain can be weakened by evanescent field absorption of Pt. Similar electric field enhancement is observed in Ni-filled nanotube as well.

Assuming there are enough molecules so that every hot-spot can contribute to SERS measurement, it is possible to calculate the total SERS signals by $\Sigma |E_i|^4$, where $E_i$ is the electric field in each hot spot. The total SERS signals of these four devices are $0.8 \times 10^5$, $2.5 \times 10^6$, $1.4 \times 10^5$ and $1.3 \times 10^5$ a.u., respectively. It is seen that device 2 will be able to provide more than 10× higher SERS signals than device 3 and 4. However, in reality, the SERS signals from hot-spots at the bottom to the nanotubes are more difficult to collect due to NP scattering. The comparison of single-side and dual-side Ag NP coated segments in the nanotubes is Table 2, below.

TABLE 2

Comparison of single-sided and double-sided Ag NPs

| | Single-sided Ag NPs | Dual-sided Ag NPs |
|---|---|---|
| Substrate for Ag NPs | Silica coated solid nanowire segments (Ni or Pt) | Hollow silica nanotubes |
| Ag NPs coating condition | Same conditions as described in the main text | |
| Ag NPs on the outer surface of silica | Same characteristics: particle and junction size | |
| Ag NPs on the inner surface of silica | none | large arrays exist as revealed by FIB/SEM, the particle size and junction cannot be accurately determined |
| SERS testing condition | See setup and procedure of SERS characterization | |
| SERS enhancement | EF = $7.2 \times 10^9$ (8 × sample on the Ni embedded sections) | More than two time stronger than that from single-sided Ag NPs |

Moreover, it was noted that the thickness of silica also affects the enhancement of SERS. The inventors observed near-field enhancement effect on nanotubes with silica coating ranging from 70 to 150 nm. However, when the thickness of silica was increased to 300 nm, the near-field enhancement effect was not observed, which may be attributed to the reduced plasmonic coupling between Ag NPs across the silica shell.

Figure 19A:
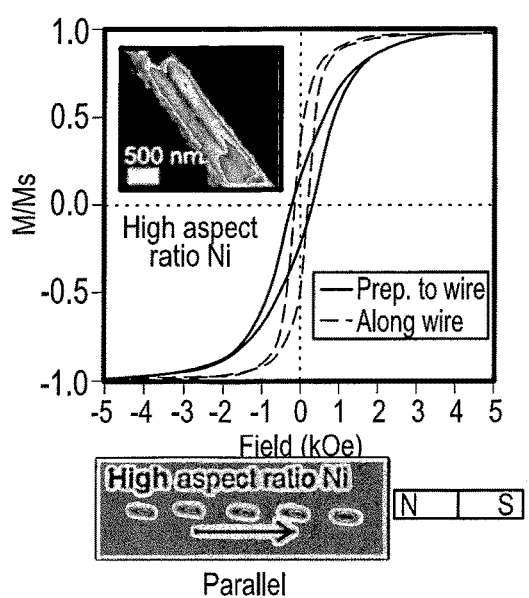
FIGS. 19A and 19B show that magnetic anisotropy can be readily tuned by the aspect ratio of magnetic Ni embedment as shown in the hysteresis loops for Ni with (19A) high and (19B) low aspect ratios, respectively. The overlapped images show nanotubes transported parallel or perpendicular to the magnetic field due to their unique anisotropies. The speed of nanotubes is 5-7 μm/sec.
Figure 19B:
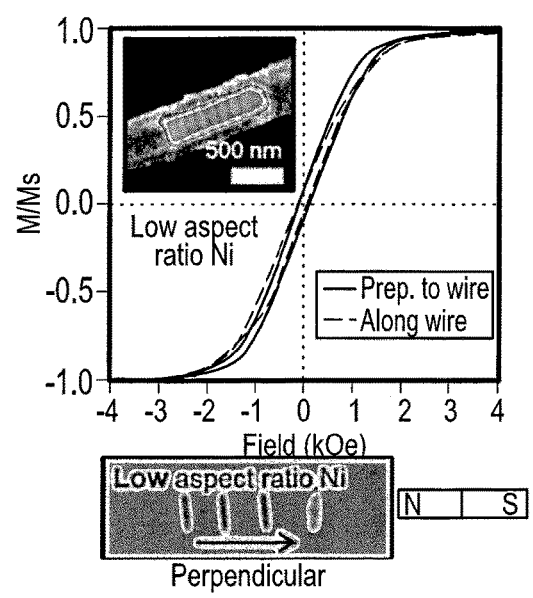

Magnetic characterization. Not only plasmonically sensitive, the unique nanotubes also offered tunable magnetic properties for controlled manipulation. The magnetic anisotropy of Ni segment is dominated by its shape anisotropy[9] as opposed to its weak crystalline anisotropy. When the aspect ratio of Ni segment is high, e.g. 10/1 (Ni length 3 um, diameter 300 nm), the anisotropy direction and the easy axis is along the nanotube long axis as measured by Vibrating Sample Magnetometry (VSM) (FIG. 19A). A hysteresis loop along magnetic easy axis demonstrates higher magnetic remanence and squareness than those measured perpendicular to the nanotubes. When the aspect ratio of the Ni segments is below 1, e.g. a stack of thin Ni disks with diameters of 300 nm and thickness of 30 nm, magnetic anisotropy is generally transverse to the nanotubes with essentially zero remanence due to the anti-parallel coupling of the magnetizations in neighboring nanodisks (FIG. 19B). This fascinating way of controlling the magnetic anisotropy has been vividly demonstrated by manipulating nanotubes in suspension with a magnetic field. As shown in FIGS. 19A and B, nanotubes with magnetic anisotropy along the long axis align with the magnetic field during transport, but those with transverse magnetic anisotropy align perpendicular to the magnetic field. The transport speed was 2-7 μm/s, which can be controlled by the magnetic field gradient.

Figure 20A:
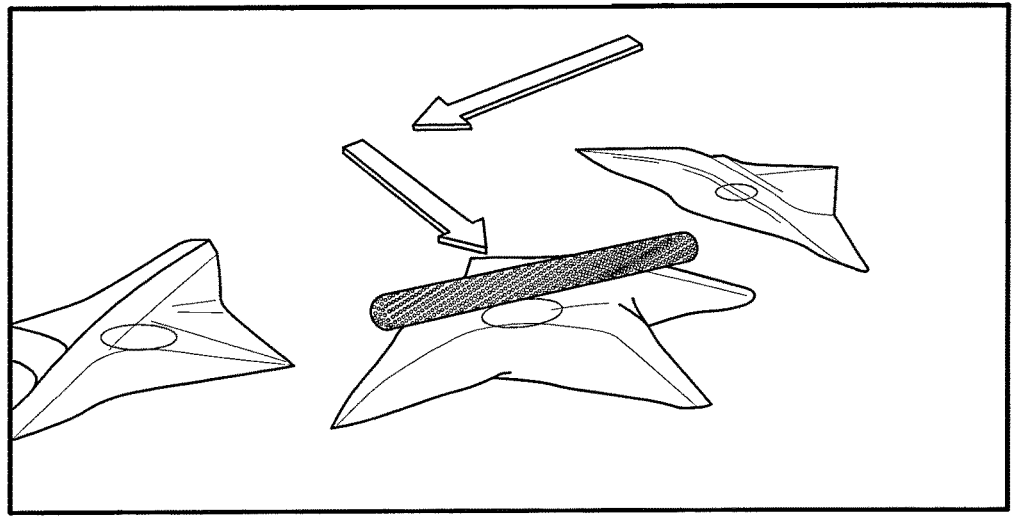
FIGS. 20A and 20B show the transport a nanotube to a single CHO cell amidst many.
Figure 20B:
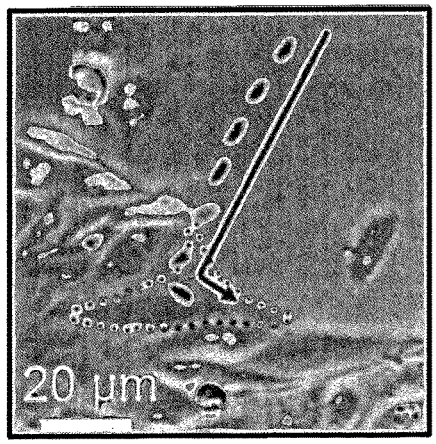
Figure 20C:
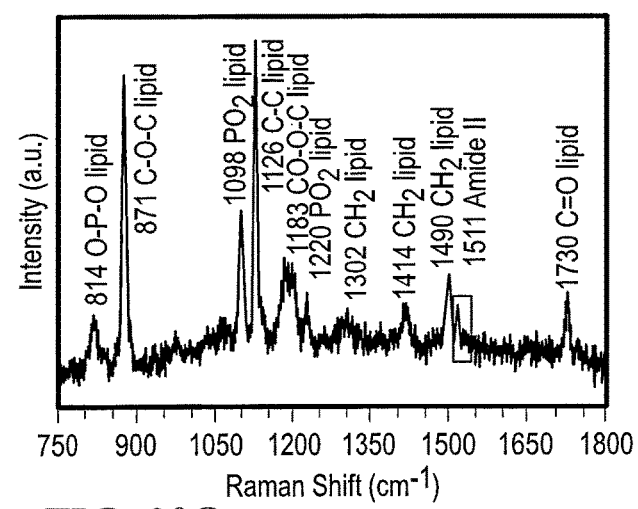
FIG. 20C shows the SERS spectrum from the CHO cell membrane is dominated by lipid contribution, and a few peaks can be assigned to protein (blue bar).

Single-cell bioanalysis. Although single complex biological samples can be investigated with standard Raman microscopy, a detailed investigation of specific components on the cell surface is not possible with this approach[19]. The used of the bifunctional nanotubes in revealing the membrane composition of a single Chinese Hamster Ovary (CHO) cell amidst many was shown. CHO cells were selected because they are widely used in biological research, especially in studies of genetics, toxicity screening, gene expression, and expression of recombinan proteins. Here, leveraging the unique bifunctionality of the nanotubes, it was possible to precisely transport a nanotube to a specific living CHO cell amidst many and detected its membrane chemistry with SERS spectroscopy. A PM nanotube was transported and aligned in the direction of the magnetic field and precisely landed on the membrane of a CHO cell (overlapped images in FIGS. 20A-20B). From SERS spectra (FIG. 20C), which was taken from the nanotube with an integration time of 5 seconds, shows strong characteristic peaks of lipids[7, 19-20]. The peak position 1511 cm$^{-1}$ can be assigned to amide II, which is from protein (blue bar in FIG. 20C). The results revealed that the cell membrane in contact with the nanotube consists mostly lipids and some protein molecules, which is consistent with real cell membrane composition[19]. Without nanotubes, no Raman signals can be detected from the cell, this clearly demonstrating the highly desirable bifunctionality of the nanotubes for precision and ultrasensitive single-cell bio-analysis. This technique is generally applicable to any adhesive live cells. It can be readily applied to hamster cells as well as to mouse or human cells.

In summary, the inventors have successfully designed and synthesized a unique type of near-field enhanced bifunctional PM-active nanostructure that include a hosting silica nanotube, a magnetic segment embedded within the nanotube, and Ag NPs uniformly coated on the dual surfaces of the nanotube. By controlling the fabrication conditions, both the diameter and junction of Ag NPs can be precisely controlled for ultrasensitive molecular sensing. The 3-D FDTD simulation of E-field enhancement agrees with the experimental results. Higher SERS intensity is found on hollow than the solid parts of the PM nanotubes, and it is confirmed to be from the near field coupling between the inner and outer layer of Ag NPs. The embedded nanomagnets with tunable magnetic anisotropy allow flexible manipulation of the nanotubes with external magnetic fields. Such bifunctional nanostructures can be transported to a living Chinese hamster ovary cell amidst many other cells to reveal the membrane composition. The PM nanotubes are suitable for single-cell bioanalysis as well as various biological applications, such as biochemical sensing, magnetic manipulation, separation, MRI contrast, and biosubstance delivery.

Fabrication of plasmonic-magnetic nanotubes: A series of strategies were implemented to synthesize the unique bifunctional nanotubes using the above approach. In brief, the multisegment Ag/Ni/Ag nanowires were fabricated by electrodeposition in 1, nanoporous anodized aluminum oxide (AAO) templates as reported elsewhere.[11, 21] In brief, a Cu layer of about 500 nm in thickness was thermal evaporated onto the back of the template to seal the pores and serve as the working electrode in a three-electrode electrodeposition system. The electrodeposition of metal materials gradually fill the bottom of the nanopores working electrode to form nanowires.[16] Finally, the AAO template was dissolved in 2M NaOH solution to release the freestanding nanowires. The amount of electric charge passing through the circuit controls the length of nanowires to 7 nm.[22] The pore size of nanoporous template controls the diameters of the nanowires from 20 to 400 nm, with different compositions along the lengths (e.g. Ag/Ni/Ag nanowires) (FIG. 13A), and prepared 300 nm diameter 3/3/3 μm Ag/Ni/Ag nanowires (−1.1 V for Ag and −1V for Ni).

Next, the Ag/Ni/Ag nanowires were used as templates for fabricating Ni-embedded silica nanotubes. In this example, an amorphous silica layer was coated on the surface of the Ag/Ni/Ag nanowires. Silica was used due to its porous structure with a high surface area, biocompatible properties, and drug carrier capability[10a]. Here, it also serves as a support substrate for plasmonic Ag NPs. The reaction was accomplished by hydrolysis of tetraethyl orthosilicate for 2-5 hours with a controlled thickness of a few to hundreds of nanometers[10]. Next, the Ag segments were selectively etched with a mixture (4:1:1) of methanol (99%), hydrogen peroxide (30%), and ammonia hydroxide (28~30% as $NH_3$), which result in Ni-embedded nanotubes as shown in FIG. 13B.

Finally, arrays of plasmonic Ag NPs were uniformly synthesized on the surface of silica nanotubes by reduction of Ag ions with PVP (10 mL, $2.5 \times 10^{-5}$ M in ethanol) from a mixed solution of silver nitrate (0.06 M, 400 µl) and ammonia hydroxide (0.12 M, 400 µl) at 70° C. for 7 hours.

Cell culture and reagents: Chinese hamster ovary (CHO) cells (ATCC) were cultured in RPMI medium (Invitrogen) supplemented with 10% Fetal Bovine Serum and 1% penicillin-streptomycin (Invitrogen). Cells were maintained in a humidified 37° C., 5% $CO_2$ incubator. Before the experiment being conducted, CHO cells were washed by Phosphate Buffered Saline (PBS) followed by addition of nanotubes (dispersed in PBS).

Estimation of SERS enhancement factor: The SERS EF was calculated by following a commonly used method reported elsewhere[23] as given below:

$$EF = \frac{I_{SERS}/N_{SERS}}{I_{RS}/N_{RS}}, \quad \text{Eq. S1}$$

$N_{SERS}$ is the number of adsorbed molecules enhanced by SERS substrate in the detection volume, $I_{SERS}$ is the corresponding SERS intensity, $N_{RS}$ is the average number of molecules excited without surface enhancement, and $I_{RS}$ is its corresponding Raman intensity.

The values of $I_{RS}$ were obtained from 0.1 M BPE in ethanol. Here a BPE was selected as the detection probe because it is a non-resonant chemical, which is widely used for estimation of EF of SERS substrates.[23a, 24] A low laser power of 30 µW (532 nm) was chosen to avoid intensity saturation as well as photo-degradation of the analyte. The laser was fully focused into the BPE solution via a 50× objective. A Raman spectrum with an intensity ($I_{RS}$) of 1.06 counts/second (at 1200 cm$^{-1}$) was obtained.

$N_{RS}$ is given by $N_{RS}=V_{scat}C_{BPE}N_A$, where $V_{scat}$ is the scattering volume of BPE that contributes to the measured Raman signal, $C_{BPE}$ is the concentration of the BPE (0.1 M), and $N_A$ is Avogadro's number. $V_{scat}$ is given by $V_{scat}=A_{obj}H_{obj}$, where $A_{obj}=\pi (0.5\ \mu m)^2$ is the area of the laser spot from the 50× objective and $H_{obj}$ is the effective height of the detection volume of BPE. Therefore, $N_{RS}=A_{obj}H_{obj}C_{BPE}N_A$. The $H_{obj}$ was determined by using the method reported elsewhere.[25] In brief, the measurement was carried out by moving a silicon <100> wafer with 1 µm increment through the focal plane of the objective and collecting the intensity of Si Raman signal at 520 cm$^{-1}$ at each point. $H_{obj}=11.6$ µm was obtained by integrating the intensity of Raman signal with distance and then dividing by the highest measured signal. By using this method, $V_{scat}$ was determined to be 15.3 µm$^3$.

Therefore, the total number of molecules ($N_{RS}$) can be determined to be:

$N_{RS}=0.1$ mol/L×11.6 µm$^3$×$6.02 \times 10^{23}$ molecules/mol=$7.0 \times 10^8$ molecules.

To measure the value of $I_{SERS}$ from the nanotubes (inner radius of 150 nm, 70 nm $SiO_2$ coating, total radius of 220 nm), the nanotubes were dispersed on a glass substrate, dried in air, and then incubated them in 1 mM BPE in ethanol for 10 min. The nanotubes were then rinsed with pure ethanol to remove excess molecules and dried in air. $I_{SERS}$ was measured from the section of nanotubes with solid Ni embedment with 532 nm laser (diameter $D_{laser}=1$ µm). It is because in such an area only a monolayer of Ag NPs was on the surface compared with those of the hollow sections of nanotubes with double layers of Ag NPs, from which SERS EF can be more rigorously calculated. $I_{SERS}$ was obtained to be 12500 counts/second (at 1200 cm$^{-1}$). To know the total number of hotspot-enhanced molecules that contribute to such a SERS signal, the effective area of nanotubes was estimated ($A_{eff}$) excited by the laser. Noting that the nanotubes are cylindrical, assuming an effective factor (f) for calculations of the effective area $A_{eff}$, which is proportional to the radius of the nanotubes (f~R), then $A_{eff}=fD_{laser}2R$. In previous study, f for nanocapsules of 300 nm in radius (150 nm $SiO_2$ coating) was approximated as $\frac{1}{3}$[11]. Here, the f for the nanocapsules with smaller radius of 220 nm (70 nm $SiO_2$ coating) can be approximated as $$f = \frac{1}{3}\frac{R_{220}}{R_{300}}$$
$$= 0.24.$$

Then, the $A_{eff}=0.24 \times 1$ µm$\times 2 \times 220$ nm=0.106 µm$^2$. Next, consider molecules residing in the 1.56 nm$^3$ volume of the ~1.16±0.5 nm narrow junction contributed the most to the Raman intensity (only junctions<2 nm). There were approximately 9 molecules/junction for a close packed monolayer of BPE (3 Å×6 Å×10 Å/molecule).[23a] The following is obtained:

$N_{SERS} = 0.106$ µm$^2 \times 1200$ hotspots/µm$^2 \times 9$ molecules/hotspot =

1145 molecules, and, $$EF = \frac{I_{SERS}/N_{SERS}}{I_{RS}/N_{RS}}$$
$$= \frac{12500/1145}{1.06/(7.0 \times 10^8)}$$
$$= 7.2 \times 10^9.$$

TABLE 3

Summarized particle size, particle density, average hotspot/junction size (<2 nm) and density, and SERS intensity for different samples.

| Samples | 0.2× | 6× | 8× | 12× |
|---|---|---|---|---|
| Particle size (nm) | 10.2 ± 2.4 | 18.7 ± 4.0 | 24.8 ± 6.7 | 24.7 ± 6.5 |
| Density/(µm$^2$) | 70 | 2050 | 1650 | 1500 |
| Junction density (<2 nm)/(µm$^2$) | 0 | 280 | 1200 | 1000 |

TABLE 3-continued

Summarized particle size, particle density, average hotspot/junction size (<2 nm) and density, and SERS intensity for different samples.

| Samples | 0.2× | 6× | 8× | 12× |
|---|---|---|---|---|
| Average junction size(<2 nm) (nm) | N/A | 1.40 | 1.16 | 1.20 |
| Normalized SERS Intensity (a.u.) | 0 | 0.25 | 1 | 0.68 |

The present inventors have rotated the plasmonic nanotubes as motors, which can release molecules in a tunable fashion while simultaneously detect them (the higher the rotation speed, the higher the release rate).

Fabrication of Nanowires.

In a three-electrode setup, Cu layer on the back of nanoporous anodized aluminium oxide (AAO) template, Pt mesh, and a Ag/AgCl electrode serve as a working electrode, a counter electrode, and a reference electrode, respectively. The growth of the nanowires commences at the bottom of nanopores at the working electrode. The amount of electric charges passing through the circuit controls the length of each segment. As a result, arrays of nanowires, with a structure of 100-1000-nm-long Ni segment sandwiched between two 350-500-nm-long Au segments, were synthesized and suspended in DI water.

Creation of rotating E-fields.

Rotating AC E-fields can be generated in the center of quadruple microelectrodes by applying four AC voltages with 90° C. sequential phase shifts on the four sub-electrodes.

Figure 21A:
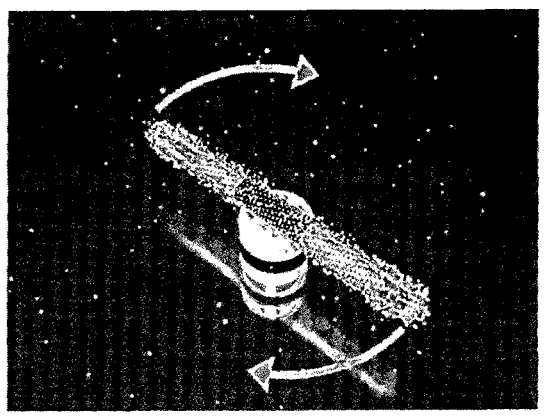
FIGS. 21A and 21B show a controlled biochemical release by nanomotors.
Figure 21B:
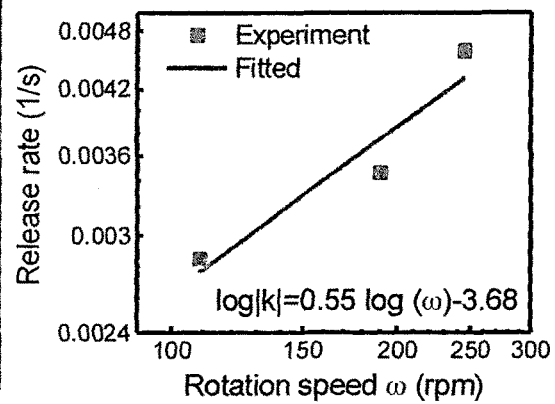

Controlled Biochemical Release from Nanomotors:

Finally, the applications of nanowire motors were demonstrated for rotation-controlled biochemical release as shown in FIG. 21A. In this study, Nile blue molecules were used to demonstrate controllable molecular release by mechanically rotating nanomotors, considering their large Raman scattering cross-sections for optical characterization and wide usage in tagging biomolecules for biological study. By functionalizing the surface of nanowire rotors with surface-enhanced-Raman-scattering sensitive Ag nanoparticles, the inventors detected time-dependent release of Nile blue molecules from single rotating nanomotors using Raman spectroscopy. The release rate (k) monotonically increases with the rotation speeds of nanomotors (FIG. 21B). Biochemical release from nanoparticles can be controlled predictably by mechanical rotation, which is a completely new actuation mechanism for biochemical release. The fundamental principle can be attributed to thickness change of electric-double layers, which will be studied elsewhere. Such molecule release mechanism is applicable not only to Raman-sensitive molecules but also to any biochemicals of interests, such as drugs, cytokine, DNA, antigens, and antibodies.

The demonstration of nanomotors for biochemical release as shown above is still in a non-bioenvironment. The present invention can also be used in other applications and using nanomotors in any biosetting. The inventors successfully employed electric tweezers to deliver drug-functionalized nanowires to a single live cell amidst many and characterized responses from the cell, which proved the compatibility of electric tweezers with the actual bioenvironment. The present invention can be used for the assembling and actuation of nanomotors in a biosetting, using the same technique as the electric tweezers. Nanomotors are a unique tool for tunable release of biochemicals to a single live cell, which is important for understanding the fundamental signal transduction on single-cell levels. It is possible to position magnetic bearings in the vicinity of selected live cells for assembling nanomotors. To do so a magnetic nanobearings is fabricated on a wafer scale. Growing cells (typically 10 μm) on such substrates and controlling the density of the magnetic bearings, one can always find a few magnetic bearings close to a live cell for nanomotor assembling. Optimization can include the amount of chemicals loaded on the nanomotors and the control of distance of the nanomotors to the cell. Various biochemicals of interests can be used, as taught herein. The nanomotors can release chemicals to the vicinity of cells, while cannot deliver chemicals into cells as shown by other reports. Also, the devices and methods taught herein are suitable for single/few cell study in an in-vitro setting. It is not applicable to in-vivo study. Overall, the inventors demonstrate the tunable biochemical release using nanomotors in a simple aqueous environment. The present inventors show the tunable release of biochemicals from nanomotors can be used to study single cell stimulation, cell-cell communication, and system biology. The inventors demonstrated a controlled biochemical release in a simple non-biosetting, and present a new mechanical approach for tuning releasing rate of biochemicals from nanoparticles. The present invention can be used, for example, in NEMS, bioNEMS, microfluidics, and lab-on-a-chip architectures.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Example 1

[1] a) E. Bailo, V. Deckert, Chem. Soc. Rev. 2008, 37, 921.
b) J. M. McMahon, A. I. Henry, K. L. Wustholz, M. J. Natan, R. G. Freeman, R. P. Van Duyne, G. C. Schatz, Anal Bioanal Chem 2009, 394, 1819.
c) J. P. Camden, J. A. Dieringer, Y. Wang, D. J. Masiello, L. D. Marks, G. C. Schatz, R. P. Van Duyne, J. Am. Chem. Soc. 2008, 130, 12616.
d) L. Qin, S. Zou, C. Xue, A. Atkinson, G. C. Schatz, C. A. Mirkin, Proc. Nat. Acad. Sci. USA 2006, 103, 13300.
[2] Campion, P. Kambhampati, Chem. Soc. Rev. 1998, 27, 241.
[3] a) J. Kneipp, H. Kneipp, M. McLaughlin, D. Brown, K. Kneipp, Nano Lett. 2006, 6, 2225.
b) T. Kang, S. M. Yoo, I. Yoon, S. Y. Lee, B. Kim, Nano Lett. 2010, 10, 1189.
[4] a) S. L. Kleinman, E. Ringe, N. Valley, K. L. Wustholz, E. Phillips, K. A. Scheidt, G. C. Schatz, R. P. Van Duyne, J. Am. Chem. Soc. 2011, 133, 4115.
b) H. X. Xu, Appl. Phys. Lett. 2004, 85, 5980.
[5] X. M. Qian, S. M. Nie, Chem. Soc. Rev. 2008, 37, 912.
b) S. Nie, S. R. Emory, Science 1997, 275, 1102.
[6] M. Moskovits, Nature 2011, 469, 307.
[7] A. M. Michaels, J. Jiang, L. Brus, J. Phys. Chem. B 2000, 104, 11965.
[8] a) C. Liusman, S. Z. Li, X. D. Chen, W. Wei, H. Zhang, G. C. Schatz, F. Boey, C. A. Mirkin, Acs Nano 2010, 4, 7676.
b) M. R. Jones, K. D. Osberg, R. J. Macfarlane, M. R. Langille, C. A. Mirkin, Chem Rev 2011, 111, 3736.
c) M. J. Banholzer, L. D. Qin, J. E. Millstone, K. D. Osberg, C. A. Mirkin, Nature Protocols 2009, 4, 838.
d) L. D. Qin, S. Park, L. Huang, C. A. Mirkin, Science 2005, 309, 113.
e) G. F. Zheng, X. D. Chen, C. A. Mirkin, Small 2009, 5, 2537.
[9] L. Qin, M. J. Banholzer, J. E. Millstone, C. A. Mirkin, Nano Lett. 2007, 7, 3849.
[10] M. J. Banholzer, K. D. Osberg, S. Li, B. F. Mangelson, G. C. Schatz, C. A. Mirkin, ACS Nano 2010, 4, 5446.
[11] U. Huebner, H. Schneidewind, D. Cialla, K. Weber, M. Zeisberger, R. Mattheis, R. Moeller, J. Popp, Biophotonics: Photonic Solutions for Better Health Care Ii 2010, 7715.
[12] C. L. Haynes, R. P. Van Duyne, J. Phys. Chem. B 2001, 105, 5599.
[13] S. J. Lee, A. R. Morrill, M. Moskovits, J. Am. Chem. Soc. 2006, 128, 2200.
[14] a) M. Hu, F. S. Ou, W. Wu, I. Naumov, X. Li, A. M. Bratkovsky, R. S. Williams, Z. Li, J. Am. Chem. Soc. 2010, 132, 12820.
b) F. S. Ou, M. Hu, I. Naumov, A. Kim, W. Wu, A. M. Bratkovsky, X. Li, R. S. Williams, Z. Li, Nano Lett. 2011, 11, 2538.
[15] M. S. Schmidt, J. Hubner, A. Boisen, Adv. Mater. 2012, 24, OP11.
[16] a) D. L. Fan, R. C. Cammarata, C. L. Chien, Appl. Phys. Lett. 2008, 92, 093115.
b) D. L. Fan, F. Q. Zhu, R. C. Cammarata, C. L. Chien, Appl. Phys. Lett. 2004, 85, 4175.
c) D. L. Fan, F. Q. Zhu, R. C. Cammarata, C. L. Chien, Appl. Phys. Lett. 2006, 89, 223115.
d) D. L. Fan, F. Q. Zhu, R. C. Cammarata, C. L. Chien, Nano Today 2011, 6, 339.
e) D. Fan, Z. Yin, R. Cheong, F. Q. Zhu, R. C. Cammarata, C. L. Chien, A. Levchenko, Nature Nanotech. 2010, 5, 545.
f) D. Fan, F. Zhu, R. Cammarata, C. Chien, Phys. Rev. Lett. 2005, 94.
[17] a) S. Inaba, S. Fujino, K. Sakai, Phys. Chem. Glass.-Euro. J. Glass. Sci. Tech. Part B 2010, 51, 304.
b) D. K. Yi, S. T. Selvan, S. S. Lee, G. C. Papaefthymiou, D. Kundaliya, J. Y. Ying, J. Am. Chem. Soc. 2005, 127, 4990.
c) C. Graf, D. L. J. Vossen, A. Imhof, A. van Blaaderen, Langmuir, 2003, 19, 6693.
d) Y. F. Zhu, J. L. Shi, W. H. Shen, X. P. Dong, J. W. Feng, M. L. Ruan, Y. S. Li, Angew. Chem. Int. Edit. 2005, 44, 5083.
[18] Processed by ImageJ, http://rsbweb.nih.gov/ij/index.html.
[19] a) V. Amendola, O. M. Bakr, F. Stellacci, Plasmonics 2010, 5, 85.

b) Z. X. Liu, H. H. Wang, H. Li, X. M. Wang, Appl. Phys. Lett. 1998, 72, 1823.

[20] E. C. Le Ru, E. Blackie, M. Meyer, P. G. Etchegoin, J. Phys. Chem. C 2007, 111, 13794.

[21] E. J. Blackie, E. C. L. Ru, P. G. Etchegoin, J. Am. Chem. Soc. 2009, 131, 14466.

[22] a) S. M. Stranahan, K. A. Willets, Nano Lett. 2010, 10, 3777.

b) M. L. Weber, J. P. Litz, D. J. Masiello, K. A. Willets, ACS Nano 2012, 6, 1839.

c) S. M. Nie, S. R. Emery, Science 1997, 275, 1102.

d) D.-K. Lim, K.-S. Jeon, H. M. Kim, J.-M. Nam, Y. D. Suh, Nature Mater. 2009, 9, 60.

e) J. A. Dieringer, R. B. Lettan, 2nd, K. A. Scheidt, R. P. Van Duyne, J. Am. Chem. Soc. 2007, 129, 16249.

f) A. M. Michaels, M. Nirmal, L. E. Brus, J. Am. Chem. Soc. 1999, 121, 9932.

g) E. J. Blackie, E. C. Le Ru, P. G. Etchegoin, J. Am. Chem. Soc. 2009, 131, 14466.

[23] J. H. Gao, G. L. Liang, J. S. Cheung, Y. Pan, Y. Kuang, F. Zhao, B. Zhang, X. X. Zhang, E. X. Wu, B. Xu, J. Am. Chem. Soc. 2008, 130, 11828.

[24] X. Xu, D. Hasan, L. Wang, S. Chakravarty, R. T. Chen, D. L. Fan, A. X. Wang, Appl. Phys. Lett. 2012, 100, 191114.

Example 2

[1] a) C. S. Levin, C. Hofmann, T. A. Ali, A. T. Kelly, E. Morosan, P. Nordlander, K. H. Whitmire, N. J. Halas, Acs Nano 2009, 3, 1379.

b) S. Peng, C. H. Lei, Y. Ren, R. E. Cook, Y. G. Sun, Angew. Chem. Int. Edit. 2011, 50, 3158.

c) G. A. Sotiriou, A. M. Hirt, P. Y. Lozach, A. Teleki, F. Krumeich, S. E. Pratsinis, Chem. Mater. 2011, 23, 1985.

d) Z. C. Xu, Y. L. Hou, S. H. Sun, J. Am. Chem. Soc. 2007, 129, 8698.

e) Y. D. Jin, C. X. Jia, S. W. Huang, M. O'Donnell, X. H. Gao, Nat. Commun 2010, 1;

f) V. V. Temnov, G. Armelles, U. Woggon, D. Guzatov, A. Cebollada, A. Garcia-Martin, J. M. Garcia-Martin, T. Thomay, A. Leitenstorfer, R. Bratschitsch, Nat. Photonics 2010, 4, 107.

[2] a) Y. T. Lim, M. Y. Cho, J. K. Kim, S. Hwangbo, B. H. Chung, Chembiochem 2007, 8, 2204.

b) J. H. Gao, G. L. Liang, J. S. Cheung, Y. Pan, Y. Kuang, F. Zhao, B. Zhang, X. X. Zhang, E. X. Wu, B. Xu, J. Am. Chem. Soc. 2008, 130, 11828.

c) N. Insin, J. B. Tracy, H. Lee, J. P. Zimmer, R. M. Westervelt, M. G. Bawendi, Acs Nano 2008, 2, 197.

d) K. C. Weng, C. O. Noble, B. Papahadjopoulos-Sternberg, F. F. Chen, D. C. Drummond, D. B. Kirpotin, D. H. Wang, Y. K. Hom, B. Hann, J. W. Park, Nano Lett. 2008, 8, 2851.

e) C. Xu, J. Xie, D. Ho, C. Wang, N. Kohler, E. G. Walsh, J. R. Morgan, Y. E. Chin, S. Sun, Angew. Chem. Int. Edit. 2008, 47, 173.

f) K. Cheng, S. Peng, C. J. Xu, S. H. Sun, J. Am. Chem. Soc. 2009, 131, 10637;

g) C. J. Xu, B. D. Wang, S. H. Sun, J. Am. Chem. Soc. 2009, 131, 4216.

[3] X. M. Qian, S. M. Nie, Chem. Soc. Rev. 2008, 37, 912.

[4] N. J. Sniadecki, C. M. Lamb, Y. Liu, C. S. Chen, D. H. Reich, Rev. Sci. Instrum. 2008, 79.

[5] J. N. Anker, W. P. Hall, O. Lyandres, N. C. Shah, J. Zhao, R. P. Van Duyne, Nat. Mater. 2008, 7, 442.

[6] a) A. Hultgren, M. Tanase, C. S. Chen, D. H. Reich, IEEE Trans. Magn. 2004, 40, 2988.

b) A. Hultgren, M. Tanase, C. S. Chen, G. J. Meyer, D. H. Reich, J. Appl. Phys. 2003, 93, 7554.

[7] J. Kneipp, H. Kneipp, M. McLaughlin, D. Brown, K. Kneipp, Nano Lett. 2006, 6, 2225.

[8] a) G. Das, F. Mecarini, F. Gentile, F. De Angelis, H. G. M. Kumar, P. Candeloro, C. Liberale, G. Cuda, E. Di Fabrizio, Biosens. Bioelectron. 2009, 24, 1693.

b) Y. Jiao, J. D. Ryckman, P. N. Ciesielski, C. A. Escobar, G. K. Jennings, S. M. Weiss, Nanotech. 2011, 22.

c) J. M. Oran, R. J. Hinde, N. Abu Hatab, S. T. Retterer, M. J. Sepaniak, J. Raman Spectrosc. 2008, 39, 1811.

d) M. L. Coluccio, G. Das, F. Mecarini, F. Gentile, A. Pujia, L. Bava, R. Tallerico, P. Candeloro, C. Liberale, F. De Angelis, E. Di Fabrizio, Microelectron. Eng. 2009, 86, 1085.

[9] a) S. H. Lee, F. Q. Zhu, C. L. Chien, N. Markovic, Phys. Rev. B 2008, 77.

b) M. Chen, C. L. Chien, P. C. Searson, Chem. Mater. 2006, 18, 1595;

c) C. L. Chien, F. Q. Zhu, J. G. Zhu, Phys. Today 2007, 60, 40.

[10] a) Y. F. Zhu, J. L. Shi, W. H. Shen, X. P. Dong, J. W. Feng, M. L. Ruan, Y. S. Li, Angew. Chem. Int. Edit. 2005, 44, 5083.

b) D. K. Yi, S. T. Selvan, S. S. Lee, G. C. Papaefthymiou, D. Kundaliya, J. Y. Ying, J. Am. Chem. Soc. 2005, 127, 4990.

c) C. Graf, D. L. J. Vossen, A. Imhof, A. van Blaaderen, Langmuir 2003, 19, 6693.

[11] X. B. Xu, K. Kim, H. F. Li, D. L. Fan, Adv. Mater. 2012, 24, 5457.

[12] B. K. Park, S. Jeong, D. Kim, J. Moon, S. Lim, J. S. Kim, J. Colloid Interface Sci. 2007, 311, 417.

[13] a) S. M. Nie, S. R. Emery, Science 1997, 275, 1102.

b) K. Kneipp, Y. Wang, H. Kneipp, L. T. Perelman, I. Itzkan, R. Dasari, M. S. Feld, Phys. Rev. Lett. 1997, 78, 1667.

c) M. G. Albrecht, J. A. Creighton, J. Am. Chem. Soc. 1977, 99, 5215.

d) A. Campion, P. Kambhampati, Chem. Soc. Rev. 1998, 27, 241.

[14] a) E. C. Le Ru, E. Blackie, M. Meyer, P. G. Etchegoin, J. Phys. Chem. C 2007, 111, 13794.

b) F. S. Ou, M. Hu, I. Naumov, A. Kim, W. Wu, A. M. Bratkovsky, X. Li, R. S. Williams, Z. Li, Nano Lett. 2011, 11, 2538.

c) M. Hu, F. S. Ou, W. Wu, I. Naumov, X. Li, A. M. Bratkovsky, R. S. Williams, Z. Li, J. Am. Chem. Soc. 2010, 132, 12820.

d) M. S. Schmidt, J. Hubner, A. Boisen, Adv. Mater. 2012, 24, OP11.

[15] a) D. K. Lim, K. S. Jeon, J. H. Hwang, H. Kim, S. Kwon, Y. D. Suh, J. M. Nam, Nat. Nanotech. 2011, 6, 452.

b) J. P. Camden, J. A. Dieringer, Y. Wang, D. J. Masiello, L. D. Marks, G. C. Schatz, R. P. Van Duyne, J. Am. Chem. Soc. 2008, 130, 12616.

[16] S. Link, M. A. El-Sayed, J. Phys. Chem. B 1999, 103, 4212.

[17] L. Gunnarsson, E. J. Bjerneld, H. Xu, S. Petronis, B. Kasemo, M. Käll, Appl. Phys. Lett. 2001, 78, 802.

[18] Q. H. Wei, K. H. Su, S. Durant, X. Zhang, Nano Lett. 2004, 4, 1067.

[19] R. Böhme, M. Richter, D. Cialla, P. Rösch, V. Deckert, J. Popp, J. Raman Spectrosc. 2009, 40, 1452.

[20] J. Kneipp, B. Wittig, H. Bohr, K. Kneipp, Theor. Chem. Acc. 2010, 125, 319.

[21] a) D. Fan, F. Zhu, R. Cammarata, C. Chien, Phys. Rev. Lett. 2005, 94.

b) L. D. Qin, S. Park, L. Huang, C. A. Mirkin, Science 2005, 309, 113.
c) M. J. Banholzer, L. D. Qin, J. E. Millstone, K. D. Osberg, C. A. Mirkin, Nat.e Protoc. 2009, 4, 838.
d) M. J. Banholzer, J. E. Millstone, L. Qin, C. A. Mirkin, Chem. Soc. Rev. 2008, 37, 885.
e) D. L. Fan, F. Q. Zhu, X. Xu, R. C. Cammarata, C. L. Chien, Proc. Natl. Acad. Sci. 2012, 109, 9309.
[22] D. L. Fan, F. Q. Zhu, R. C. Cammarata, C. L. Chien, Nano Today 2011, 6, 339.
[23] a) M. Hu, F. S. Ou, W. Wu, I. Naumov, X. Li, A. M. Bratkovsky, R. S. Williams, Z. Li, J. Am. Chem. Soc. 2010, 132, 12820.
b) M. S. Schmidt, J. Hubner, A. Boisen, Adv. Mater. 2012, 24, OP11.
[24] F. S. Ou, M. Hu, I. Naumov, A. Kim, W. Wu, A. M. Bratkovsky, X. Li, R. S. Williams, Z. Li, Nano Lett. 2011, 11, 2538.
[25] E. J. Smythe, M. D. Dickey, J. M. Bao, G. M. Whitesides, F. Capasso, Nano Lett. 2009, 9, 1132.
[26] Fan, D. L., Yin, Z. Z., Cheung, R., Zhu, F. Q., Cammarata, R. C., Chien, C. L. & Levchenko, A. Sub-cellular-resolution delivery of a cytokine via precisely manipulated nanowires, *Nature Nanotech.* 5, 545-551 (2010).

What is claimed is:

1. A method of making a plasmonic-magnetic nanocapsule comprising:
   a) forming a silica nanotube comprising a magnetic material embedded within the silica nanotube, wherein the magnetic material comprises a segmented metallic rod, wherein the segmented rod comprises segments of silver or gold, and segments of nickel;
   b) layering at least a portion of the outer surface of the silica nanotube with metallic nanoparticles;
   to provide a plasmonic-magnetic nanocapsule.

2. The method of claim 1, wherein the nanocapsule has a diameter from 100 nm to 0.01 cm.

3. The method of claim 1, wherein the metallic rod is formed using electrodeposition.

4. The method of claim 1, wherein the metallic rod comprises nickel or platinum.

5. The method of claim 1, wherein the silica nanotube is formed by coating the metallic rod with amorphous silica.

6. The method of claim 5, wherein the coating comprises orthosilicate hydrolysis.

7. The method of claim 1, wherein the silica layer has a thickness from 100 nm to 1 µm.

8. The method of claim 1, wherein the silica layer has a thickness from 70 nm to 150 nm.

9. The method of claim 1, comprising coating the segmented metallic rod with amorphous silica followed by removing at least one segment.

10. The method of claim 9, wherein the at least one segment of the metallic rod is removed by etching.

\* \* \* \* \*